US010101346B2

(12) United States Patent
Koike et al.

(10) Patent No.: US 10,101,346 B2
(45) Date of Patent: Oct. 16, 2018

(54) SAMPLE ANALYZER, TRANSPORTATION APPARATUS, AND METHOD

(71) Applicant: SYSMEX CORPORATION, Kobe-shi, Hyogo (JP)

(72) Inventors: Hiroki Koike, Kobe (JP); Yousuke Matsui, Kobe (JP); Go Senda, Kobe (JP); Hiroo Tatsutani, Kobe (JP); Yuichiro Ohmae, Kobe (JP); Atsushi Kumagai, Kobe (JP); Tomoyuki Asahara, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 116 days.

(21) Appl. No.: 15/166,806

(22) Filed: May 27, 2016

(65) Prior Publication Data

US 2016/0349279 A1 Dec. 1, 2016

(30) Foreign Application Priority Data

May 29, 2015 (JP) ................................. 2015-110897

(51) Int. Cl.
*G01N 35/00* (2006.01)
*G01N 35/02* (2006.01)
(Continued)

(52) U.S. Cl.
CPC ... *G01N 35/00584* (2013.01); *G01N 35/0095* (2013.01); *G01N 35/021* (2013.01);
(Continued)

(58) Field of Classification Search
CPC ......... G01N 35/00584; G01N 35/0095; G01N 35/021; G01N 35/026; G01N 2035/00277;
(Continued)

(56) References Cited

U.S. PATENT DOCUMENTS

| 2005/0186113 A1 | 8/2005 | Koike et al. |
| 2009/0035873 A1* | 2/2009 | Shibata .................... G01N 1/38 436/179 |

(Continued)

FOREIGN PATENT DOCUMENTS

| JP | 2001-153872 A | 6/2001 |
| JP | 2001-159634 A | 6/2001 |
| JP | 2011-052982 A | 3/2011 |

*Primary Examiner* — Benjamin R Whatley
(74) *Attorney, Agent, or Firm* — Metrolexis Law Group, PLLC

(57) ABSTRACT

In accordance with embodiments, a transport mechanism transports a first sample container to a sample aspiration position. A setting part may set a second sample container, that accommodates a sample to be measured, with priority over a measurement of a sample in a first sample container. A nozzle may be capable of moving a sample from a first sample container at a sample aspiration position, and aspirating the sample from the second sample container. A detector may detect components of the sample. A controller may control a transport mechanism such that the first sample container moves to a position distant from the sample aspiration position, when the first sample container has been transported and when sample aspiration of the second sample container is required. A controller may execute control to move the nozzle above the sample aspiration position in state in which the first sample container is distant from the sample aspiration position.

13 Claims, 18 Drawing Sheets

(51) Int. Cl.
*G01N 35/04* (2006.01)
*G01N 35/10* (2006.01)

(52) U.S. Cl.
CPC . *G01N 35/026* (2013.01); *G01N 2035/00277* (2013.01); *G01N 2035/0406* (2013.01); *G01N 2035/0415* (2013.01); *G01N 2035/0475* (2013.01); *G01N 2035/106* (2013.01)

(58) Field of Classification Search
CPC ... G01N 2035/0406; G01N 2035/0415; G01N 2035/0475; G01N 2035/106
See application file for complete search history.

(56) References Cited

U.S. PATENT DOCUMENTS

| | | | |
|---|---|---|---|
| 2011/0076780 A1* | 3/2011 | Yamato | G01N 35/026 436/174 |
| 2012/0088293 A1* | 4/2012 | Hamada | G01N 35/026 435/287.1 |

* cited by examiner

SAMPLE ANALYZER, TRANSPORTATION APPARATUS, AND METHOD

CROSS REFERENCE TO RELATED APPLICATION

This application claims priority from prior Japanese Patent Application No. 2015-110897, filed on May 29, 2015, entitled "SAMPLE ANALYZER, TRANSPORTATION APPARATUS, AND METHOD", the entire contents of which are incorporated herein by reference.

BACKGROUND

The disclosure relates to a sample analyzer, a transportation apparatus, and a method.

Japanese Laid-open Patent Publication No. 2001-153872 (Patent document 1) discloses an automatic urine analyzer. The urine analyzer has a sample aspiration position on a measurement line on which a sample holding rack is transported. The automatic urine analyzer comprises a sample dispensing nozzle that moves horizontally and vertically; a sample in the sample holding rack at the sample aspiration position is aspirated by moving the sample dispensing nozzle to the sample aspiration position, the sample dispensing nozzle that has aspirated the sample is moved to a dispensing position, and the sample is discharged. Moreover, the automatic urine analyzer comprises an urgent sample holder in order to measure samples requiring urgent measurement. When performing urgent measurements, the automatic urine analyzer moves the sample dispensing nozzle to the urgent sample holder and aspirates a sample set in the urgent sample holder by using the sample dispensing nozzle. And then the automatic urine analyzer moves the sample dispensing nozzle that has aspirated the sample to a dispensing position passing above the sample aspiration position on the measurement line, and discharges the sample.

SUMMARY

One aspect of the embodiment is a sample analyzer, comprising: a transport part that transports a first sample container to a sample aspiration position; a setting part in which is set a second sample container that accommodates a sample to be measured with priority over measurement of a sample in the first sample container; a nozzle capable of moving for aspirating the sample from the first sample container at the sample aspiration position and aspirating the sample from the second sample container set in the setting part; a detector that detects components of the sample aspirated by the nozzle; and a controller that, if a sample aspiration from the second sample container using the nozzle is required when the first sample container has been transported to the sample aspiration position, controls the transport part such that the first sample container moves to a position distant from the sample aspiration position, and executes control such that the nozzle that has aspirated the sample from the second sample container moves above the sample aspiration position in a state in which the first sample container is distant from the sample aspiration position.

Another aspect of the embodiment is a sample analyzer, comprising: a transport part that transports a first sample container to a sample aspiration position; a setting part in which is set a second sample container that accommodates a sample to be measured with priority over measurement of a sample in the first sample container; a nozzle capable of moving for aspirating the sample from the first sample container at the sample aspiration position, and aspirating the sample from the second sample container set in the setting part; a detector that detects components of a sample aspirated by the nozzle; and a controller that, when a sample aspiration from the second sample container using the nozzle is required, determines whether the first sample container is positioned at the sample aspiration position, and when the first sample container is positioned at the sample aspiration position, controls the transport part such that the first sample container moves to a position distant from the sample aspiration position, and executes control such that the nozzle that has aspirated the sample from the second sample container moves above the sample aspiration position in a state in which the first sample container is distant from the sample aspiration position.

Another aspect of the embodiment is a transportation apparatus that comprises: a transport part that transports a first sample container to a sample aspiration position at which a sample is aspirated by a nozzle; a setting part in which is set a second sample container accommodating a sample to be measured with priority over measurement of the sample in the first sample container; and a controller that, if a sample aspiration from the second sample container using the nozzle is required when the first sample container has been transported to the sample aspiration position, controls the transport part such that the first sample container moves to a position distant from the sample aspiration position.

Another aspect of the embodiment is a sample analyzing method, that includes: (i) positioning a first sample container on a transport pathway for the first sample container; (ii) when a sample aspiration from a second sample container outside the transport pathway using a nozzle is required, moving the first sample container positioned on the transport pathway along the transport pathway so as to be positioned distant from immediately below a movement pathway of the nozzle that has aspirated the sample from the second sample container; (iii) after the first sample container has moved, moving the nozzle that has aspirated the sample from the second sample container above the transport pathway; and (iv) detecting a component of the sample aspirated by the nozzle.

DETAILED DESCRIPTION

1. Overall Configuration of a Sample Analyzer

Figure 1:
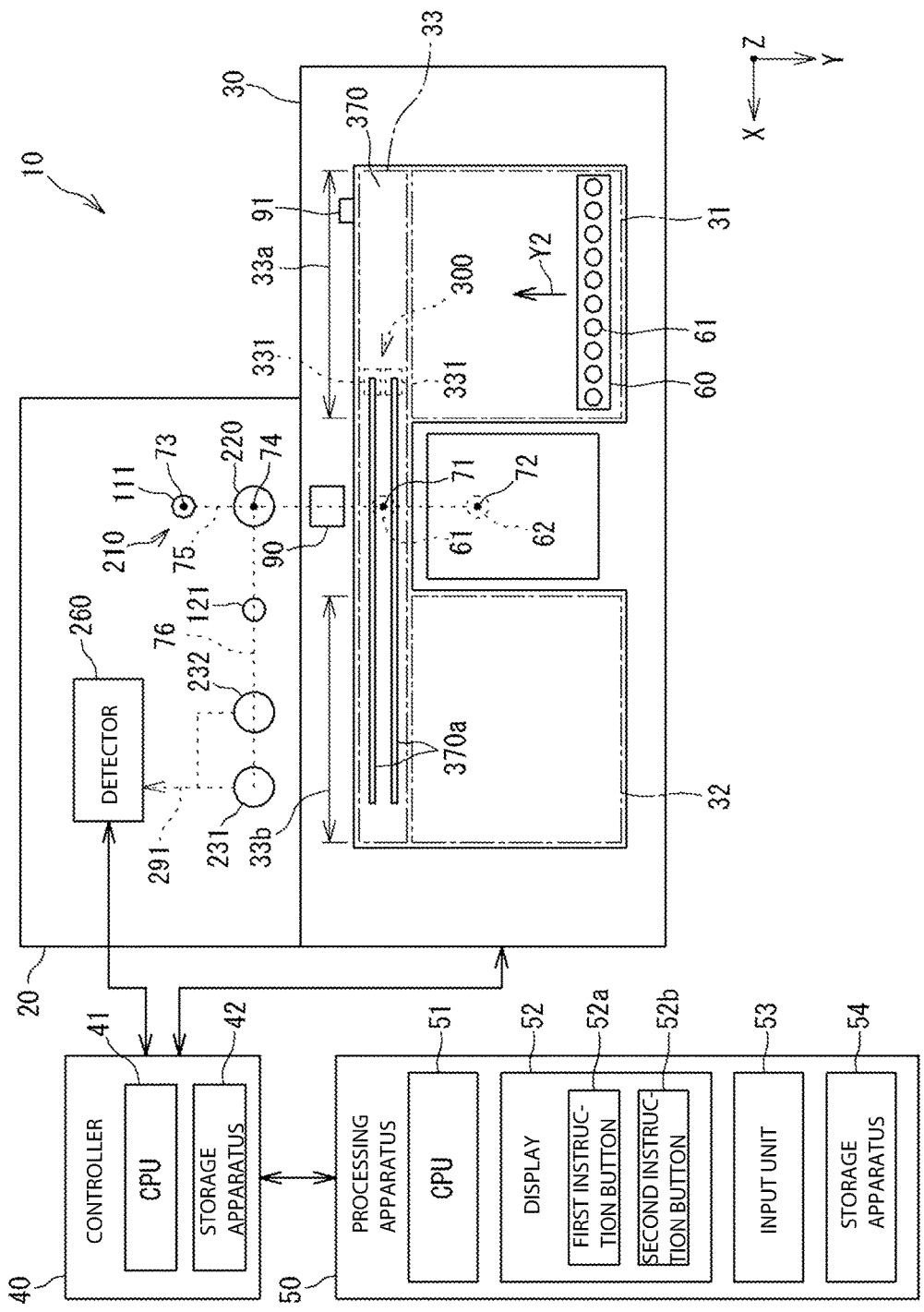
FIG. 1 is a block diagram of a sample analyzer.

Sample analyzer 10 illustrated in FIG. 1 analyzes urine samples and other samples. Sample analyzer 10 comprises measurement unit 20 and transportation apparatus 30. Measurement unit 20 performs processing related to measurement of samples. Processing related to measurement of samples include sample dispensing, preparation of specimens from samples, detection of sample components, and the like. Measurement unit 20 has dispenser 210 having first nozzle 111 and second nozzle 121 that aspirate samples, holding chamber 220, processing chambers 231, 232, and detector 260. First nozzle 111 is provided so as to be capable of moving in the longitudinal direction, illustrated as the Y direction in FIG. 1. Transportation apparatus 30 and measurement unit 20 are arranged next to each other along the longitudinal direction, which is the direction of movement of first nozzle 111. Transportation apparatus 30 transports first sample containers 61. First sample containers 61 are transported in a state of being held by rack 60. Rack 60 can hold first sample containers 61.

Sample analyzer 10 comprises controller 40. Controller 40 controls measurement unit 20 and transportation apparatus 30. Controller 40 comprises a computer, and has CPU 41 and storage apparatus 42. A computer program stored in storage apparatus 42 is executed by CPU 41 to perform processing. Controller 40 may be provided within measurement unit 20, or may be provided within transportation apparatus 30. Sample analyzer 10 comprises processing apparatus 50. Processing apparatus 50 performs processing including processing to analyze the output of detector 260. Processing apparatus 50 comprises a computer, and includes CPU 51, display 52, input unit 53, storage apparatus 54, and the like. Processing unit 51 (*2) performs processing by using CPU 51 to execute a computer program stored in storage apparatus 54. Display 52 is for example a screen display, and displays, for example, analysis results. Display 52 also performs screen display for receiving input. Input unit 54 is, for example, a keyboard or a mouse.

2. Sample Dispensing and Sample Component Detection

Dispenser 210 aspirates samples from sample containers 61, 62 in first sample aspiration position 71 or in second sample aspiration position 72, and dispenses the samples into processing chambers 231, 232. Dispenser 210 has first unit 110 that moves first nozzle 111 that aspirates and discharges samples, and second unit 120 that moves second nozzle 121 that aspirates and discharges samples.

Figure 2A:
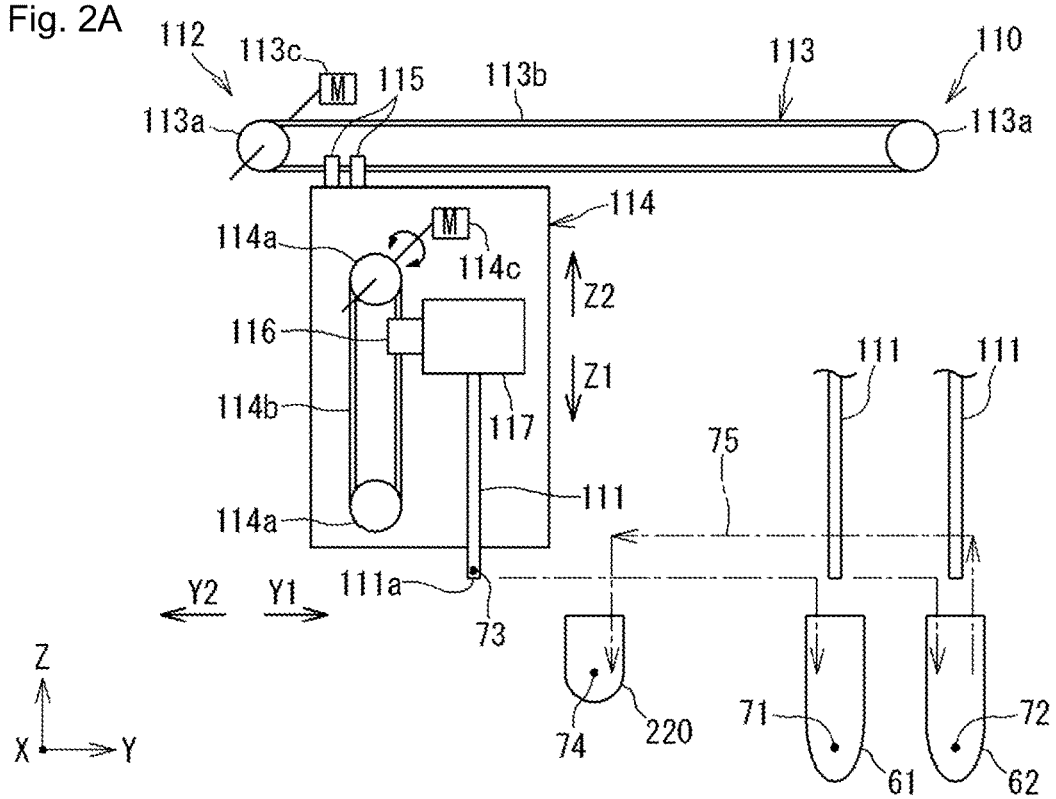
FIGS. 2A and 2B are structural views of a first unit and a second unit.

As illustrated in FIG. 2A, first unit 110 comprises first nozzle 111 and first driving unit 112 that moves first nozzle 111. First nozzle 111 aspirates a sample from aspiration opening 111a formed at the lower end, and discharges the aspirated sample from aspiration opening 111a. Aspiration and discharge of a sample via first nozzle 111 and first driving unit 112 are controlled by controller 40. First nozzle 111 is moved by first driving unit 112 from initial position 73 to first sample aspiration position 71 or to second sample aspiration position 72 for aspirating a sample. Sample aspiration positions 71, 72 are positions at which tip 111a of first nozzle 111 is to be positioned when sample aspiration is to be performed. Sample aspiration positions 71, 72 are described below.

First nozzle 111 aspirates a sample from first sample container 61 positioned at first sample aspiration position 71, or from second sample container 62 positioned at second sample aspiration position 72. In the present embodiment, the aspirated sample is a urine sample. First nozzle 111 which has aspirated a sample is moved by first driving unit 112 to discharging position 74, which is a position provided in holding chamber 220. Discharging position 74 is a position at which tip 111a of first nozzle 111 is to be positioned when sample discharging is to be performed. First nozzle 111 discharges the sample into holding chamber 220 in which discharging position 74 is provided. First nozzle 111, having discharge the sample, is returned to initial position 73 by first driving unit 112. Initial position 73 is also a standby position until the next sample aspiration.

As illustrated in FIG. 1, first sample aspiration position 71 is provided between second sample aspiration position 72 and discharging position 74. First nozzle 111 aspirates a sample from second sample container 62 at second sample aspiration position 72, and then moves above first sample aspiration position 71 toward holding chamber 220.

As illustrated in FIG. 2A, first driving unit 112 comprises first horizontal movement mechanism 113 which moves first nozzle 111 in a horizontal direction, and first vertical movement mechanism 114 which moves first nozzle 111 in a vertical direction. First horizontal movement mechanism 113 has endless belt 113b, wound about a pair of pulleys 113a. First vertical movement mechanism 114 is attached to endless belt 113b via attachment parts 115. First nozzle 111 is provided on first vertical movement mechanism 114. Pulleys 113a are rotatably driven by motor 113c. Motor 113c is controlled by controller 40. When pulleys 113a are rotatably driven, endless belt 113b rotates, and first vertical movement mechanism 114 and first nozzle 111 move in the Y1 direction or in the Y2 direction, which are first horizontal directions.

First vertical movement mechanism 114 has endless belt 114b, which is wound about a pair of pulleys 114a. First nozzle holder 117, which holds first nozzle 111, is attached to endless belt 114b via attachment part 116. Pulleys 114a are rotatably driven by motor 114c. Motor 114c is driven by controller 40. When pulleys 114a are rotatably driven, endless belt 114b rotates, and first nozzle 111, which is held by first nozzle holder 117, moves in the Z1 direction or in the Z2 direction, which are vertical directions.

As illustrated in FIG. 1, initial position 73, discharging position 74, first sample aspiration position 71, and second sample aspiration position 72 are disposed on a straight line in the Y direction, which is the longitudinal direction, in plan view. As illustrated in FIG. 2A, first nozzle 111 is moved horizontally by first horizontal movement mechanism 113 along movement pathway 75, which is a straight line connecting positions above initial position 73 and discharging position 74, above first sample aspiration position 71, and above second sample aspiration position 72. Vertical movement of first nozzle 111 from horizontal movement pathway 75 to aspirating/discharging positions 71, 72, 74 is performed by first vertical movement mechanism 114.

Figure 2B:
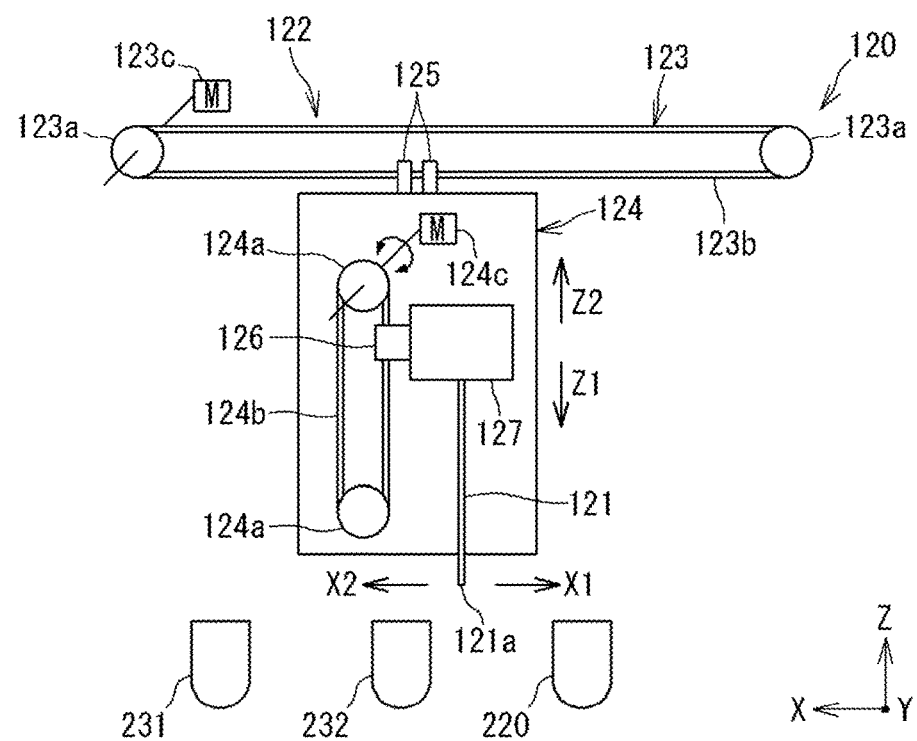

As illustrated in FIG. 2B, second unit 120 comprises second nozzle 121 and second driving unit 122, which moves second nozzle 121. Second nozzle 121 aspirates a sample from aspiration opening 121a formed at the lower end, and discharges the aspirated sample from the aspiration opening 121a. Aspiration and discharging of a sample by second nozzle 121, and second driving unit 122, are controlled by controller 40. Second nozzle 111 aspirates samples from holding chamber 220, and discharges samples to processing chambers 231, 232. More specifically, after first nozzle 111 has discharged a sample to holding chamber 220, second nozzle 121 is moved by second driving unit 122 to holding chamber 220, and aspirates a sample in holding chamber 220. Then second nozzle 121 moves to processing chambers 231, 232 and discharges the aspirated sample.

Second driving unit 122 comprises second horizontal movement mechanism 123 which moves second nozzle 121 in the horizontal directions, and second vertical movement mechanism 124 which moves second nozzle 121 in the vertical directions. Second horizontal movement mechanism 123 has endless belt 123b, wound about a pair of pulleys 123a. Second vertical movement mechanism 124 is attached to endless belt 123b via attachment parts 125. Second nozzle 121 is provided on second vertical movement mechanism 124. Pulleys 123a are rotatably driven by motor 123c. Motor 123c is controlled by controller 40. When pulleys 123a are rotatably driven, endless belt 123b rotates, and second vertical movement mechanism 124 and second nozzle 121 move in the X1 direction or in the X2 direction, which are second horizontal directions.

Second vertical movement mechanism 124 has endless belt 124b, wound about a pair of pulleys 124a. Second nozzle holder 127, which holds second nozzle 121, is attached to endless belt 124b via an attachment part 126. Pulleys 124a are rotatably driven by motor 124c. Motor 124c is controlled by controller 40. When pulleys 124a are rotatably driven, endless belt 124b rotates, and second nozzle 121, held by second nozzle holder 127, moves in the Z1 direction or in the Z2 direction, which are vertical directions.

As illustrated in FIG. 1, holding chamber 220 provided at discharging position 74 and processing chambers 231, 232 are disposed on a straight line in the X direction, which is the left-right direction, in plan view. Second nozzle 121 is moved horizontally by second horizontal movement mechanism 123 along movement pathway 76, which is a straight line connecting positions above holding chamber 220 and above processing chambers 231, 232. Vertical movement of second nozzle 121 from horizontal movement pathway 76 to chambers 220, 231, 232 is performed by second vertical movement mechanism 124.

Illustrated first driving unit 112 and second driving unit 122 move nozzles 111, 112 by a belt-driven method, but nozzles 111, 112 may be moved by other driving methods. Other driving methods that can be used are, for example, a method having a mechanism that performs movement by rotation of a threaded shaft, and a method having a mechanism in which a rotatably driven roller travels along a guide rail. Horizontal movement pathways 75, 76 of first horizontal movement mechanism 113 and second horizontal movement mechanism 123 may be curved pathways as well.

Figure 3:
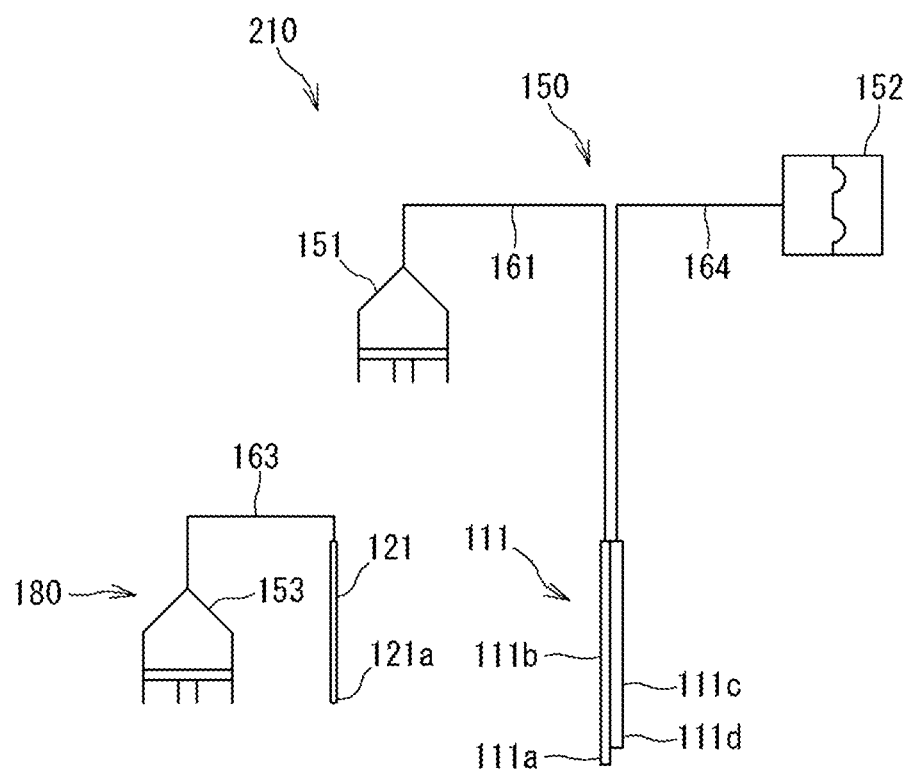
FIG. 3 is a circuit diagram of a sample aspiration circuit and a dispensing circuit.

As illustrated in FIG. 3, dispenser 210 further comprises sample aspiration circuit 150 for aspiration of samples using first nozzle 111, and dispensing circuit 180 for dispensing of samples to processing chambers 231, 232 using second nozzle 121. Sample aspiration circuit 150 and dispensing circuit 180 are configured having compressed-air circuits.

Sample aspiration circuit 150 comprises first pressure source 151 and path 161 from first nozzle 111 to first pressure source 151. First pressure source 151 is, for example, a syringe pump. Aspiration nozzle 111b and agitation nozzle 111c are integrally configured with first nozzle 111. Aspiration nozzle 111b and agitation nozzle 111c have aspiration openings 111a, 111d at their respective lower ends, and samples can be aspirated and dispensed from the aspiration openings 111a, 111d. Above-described first path 161 is connected to aspiration nozzle 111b. Sample aspiration circuit 150 further comprises second pressure source 152 and path 164 from agitation nozzle 111c to second pressure source 152. Second pressure source 152 is, for example, a diaphragm pump.

Agitation nozzle 111c agitates samples within sample containers 61, 62 prior to aspiration of samples from sample containers 61, 62. As a consequence, particles in a urine sample can be dispersed uniformly, and particle analysis results can be acquired with good precision. Through the aspiration pressure induced by second pressure source 152, samples are aspirated from sample containers 61, 62 via agitation nozzle 111c, samples are caused to flow from agitation nozzle 111c to path 164, and thereafter, discharge pressure induced by second pressure source 152 causes a sample in path 164 to again be discharged from agitation nozzle 111c to sample container 15. By repeating the aspiration and discharging performed using agitation nozzle 111c, a sample can be adequately agitated. An agitated sample is aspirated from aspiration nozzle 111b by aspiration pressure induced by first pressure source 151. A sample aspirated from aspiration nozzle 111b is discharged to holding chamber 220.

Dispensing circuit 180 comprises pressure source 153 and path 163 from second nozzle 121 to pressure source 153. Pressure source 153 is, for example, a syringe pump. Dispensing circuit 180 aspirates samples in holding chamber 220 using second nozzle 121, and dispenses the aspirated samples to processing chambers 231, 232. A sample is aspirated by aspiration pressure induced by pressure source 153, and a sample is discharged to processing chambers 231, 232 by a discharge pressure induced by pressure source 153.

Sample aspiration circuit 150 and dispensing circuit 180 include valves, not shown, for path switching.

Samples dispensed to processing chambers 231, 232 are prepared as measurement specimens in processing chambers 231, 232. Preparation of a measurement specimen is performed by mixing a sample with a reagent supplied to a processing chamber 231, 232. First measurement specimens are prepared in first processing chamber 231, and second measurement specimens are prepared in second processing chamber 232.

A first measurement specimen is obtained by mixing a urine sample and a first reagent in first processing chamber 231. First reagents are, for example, a diluent and staining solution. The staining solution, as a first reagent, includes a fluorescent dye that stains particles not having a nucleic acid. In a first measurement specimen, particles in the urine sample are stained by the staining solution. A first measurement specimen is used for detecting particles in the urine sample not having a nucleic acid, such as red blood cells and urinary casts.

A second measurement specimen is obtained by mixing a urine sample and a second reagent in second processing chamber 232. Second reagents are, for example, a diluent and staining solution. The staining solution, as a second reagent, includes a dye that stains nucleic acids. In a second measurement specimen, particles in the urine sample are stained by the staining solution. A second measurement specimen is used to detect cells in urine having a nucleic acid, such as white blood cells, epidermal cells, fungi, bacteria, atypical cells, and other cells having nucleic acids.

Measurement specimens prepared in preparation chambers 231, 232 are supplied to detector 260. Detection unit 260 detects components of samples prepared as measurement specimens. Detection unit 260 is configured using, for example, an optical detector that performs optical detection of samples. The optical detector has a flow cell. The flow cell is supplied with a first measurement specimen or a second measurement specimen by specimen introduction path 291 from processing chambers 231, 232. The optical detector irradiates the flow of a measurement specimen in the flow cell with laser light or other light, and detects light emitted from components in the measurement specimen based on the irradiated light. Light detected by the optical detector includes, for example, forward-scattered light, side-scattered light, and fluorescence.

Detection unit 260 converts detected light into an electrical signal. Detection unit 260 performs amplification, A/D conversion, and other processing of the electrical signal. A signal processing circuit of detector 260 extracts characteristic parameters of the signal after A/D conversion. Characteristic parameters are parameters used in sample analysis processing. Characteristic parameters include, for example, forward-scattered light intensity, forward-scattered light pulse width, side-scattered light intensity, fluorescence intensity, fluorescence pulse width, and fluorescence pulse area. Characteristic parameters are transmitted via controller 40 to processing apparatus 50, which performs analysis processing of components in the sample. Processing apparatus 50 analyzes components of the sample based on the received characteristic parameters.

3. Transportation Apparatus

As illustrated in FIG. 1, transportation apparatus 30 is configured to enable the transportation of rack 60, which holds first sample containers 61. Transportation apparatus 30 comprises first placement region 31, second placement region 32, and transport part 33. Rack 60 is placed in first placement region 31, where rack 60 is supplied to rack acceptance position 33a of transport part 33. Rack 60, after being ejected from rack ejection position 33b of transport part 33, is placed in second placement region 32. Transport part 33 has a transport pathway that connects rack acceptance position 33a and rack ejection position 33b. Rack 60 is placed on the transport pathway, and transport part 33 transports rack 60 along the transport pathway. Transport part 33 can move rack 60 to a desired position on the transport pathway.

First placement region 31 is formed such that racks 60 can be placed arranged in the Y direction, which is the longitudinal direction. First placement region 31 has a feed mechanism, not illustrated, and the feed mechanism transports rack 60 in the Y2 direction, which is backwards. The feed mechanism of first placement region 31 supplies rack 60 to rack acceptance position 33a.

Transport part 33 has transport mechanism 300, which moves rack 60, supplied to rack acceptance position 33a, along the transport pathway. Transport mechanism 300 is described below. In an embodiment, the length of the transport pathway of transport part 33 is set to approximately three times the length of rack 60. Hence at least one or two racks 60 can be placed simultaneously on the transport pathway of transport part 33.

Second placement region 32 is formed such that racks 60 can be placed arranged in the Y direction, which is the longitudinal direction. Second placement region 32 has a feed mechanism, not illustrated, and the feed mechanism transports rack 60 in the Y1 direction, which is forwards. The feed mechanism of second placement region 32 ejects rack 60, which is at rack ejection position 33b of transport part 33, to second placement region 32.

As illustrated in FIG. 1, first sample aspiration position 71 of first nozzle 111 is set on the transport pathway of transport part 33. First sample aspiration position 71 is set between rack acceptance position 33a and rack ejection position 33b. Transport part 33 transports rack 60 such that first sample containers 61 held by rack 60 placed at rack acceptance position 33a arrive in sequence at first sample aspiration position 71. Hence first sample containers 61 held by rack 60 are sequentially transported to first sample aspiration position 71. Samples of first sample containers 61 transported by transport part 33 to first sample aspiration position 71 are aspirated by first nozzle 111, which has been moved to first sample aspiration position 71.

Figure 8:
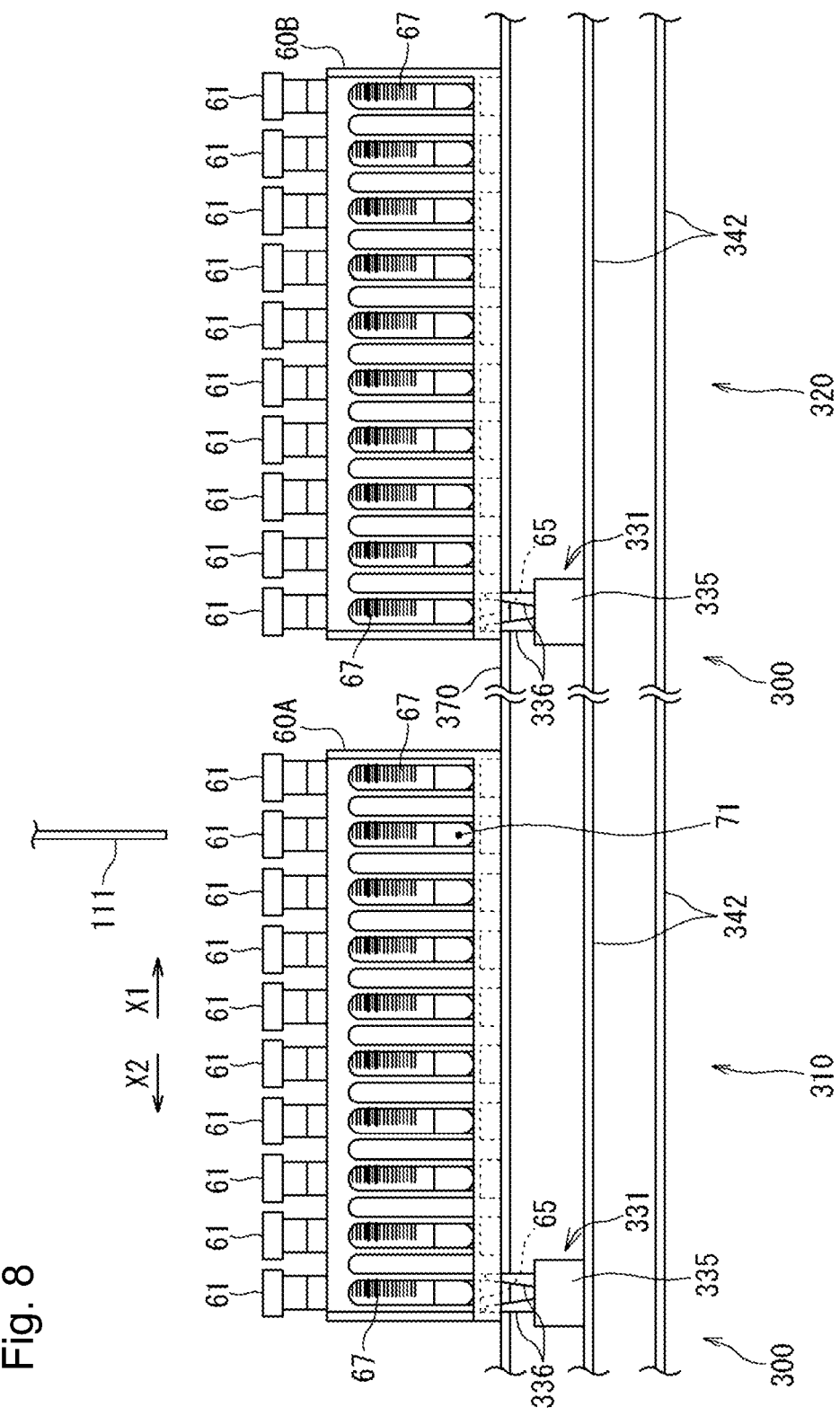
FIG. 8 is a front view of a transportation apparatus.

Sample analyzer 10 comprises readout unit 90, which reads out sample information of first sample container 61 transported to first sample aspiration position 71. As illustrated in FIG. 8, sample information is, for example, a sample number recorded in barcode 67 affixed to first sample container 61. When sample information is indicated by a barcode, readout unit 90 is a barcode reader. In this embodiment, first sample aspiration position 71 is also an information readout position at which sample information is read out by readout unit 90. Reading out of sample information by readout unit 90 is performed in advance of sample aspiration. The information readout position may be a position different from first sample aspiration position 71.

As explained above, second sample aspiration position 72 is set in front of first sample aspiration position 71. Second sample aspiration position 72 is set outside the transport pathway of transport part 33. Second sample aspiration position 72 is a position for urgent (STAT) sample aspiration. An urgent sample is a sample that is measured with priority over a sample accommodated in first sample container held by rack 60. Second sample container 62, accommodating an urgent sample, is set at second sample aspiration position 72.

Figure 4:
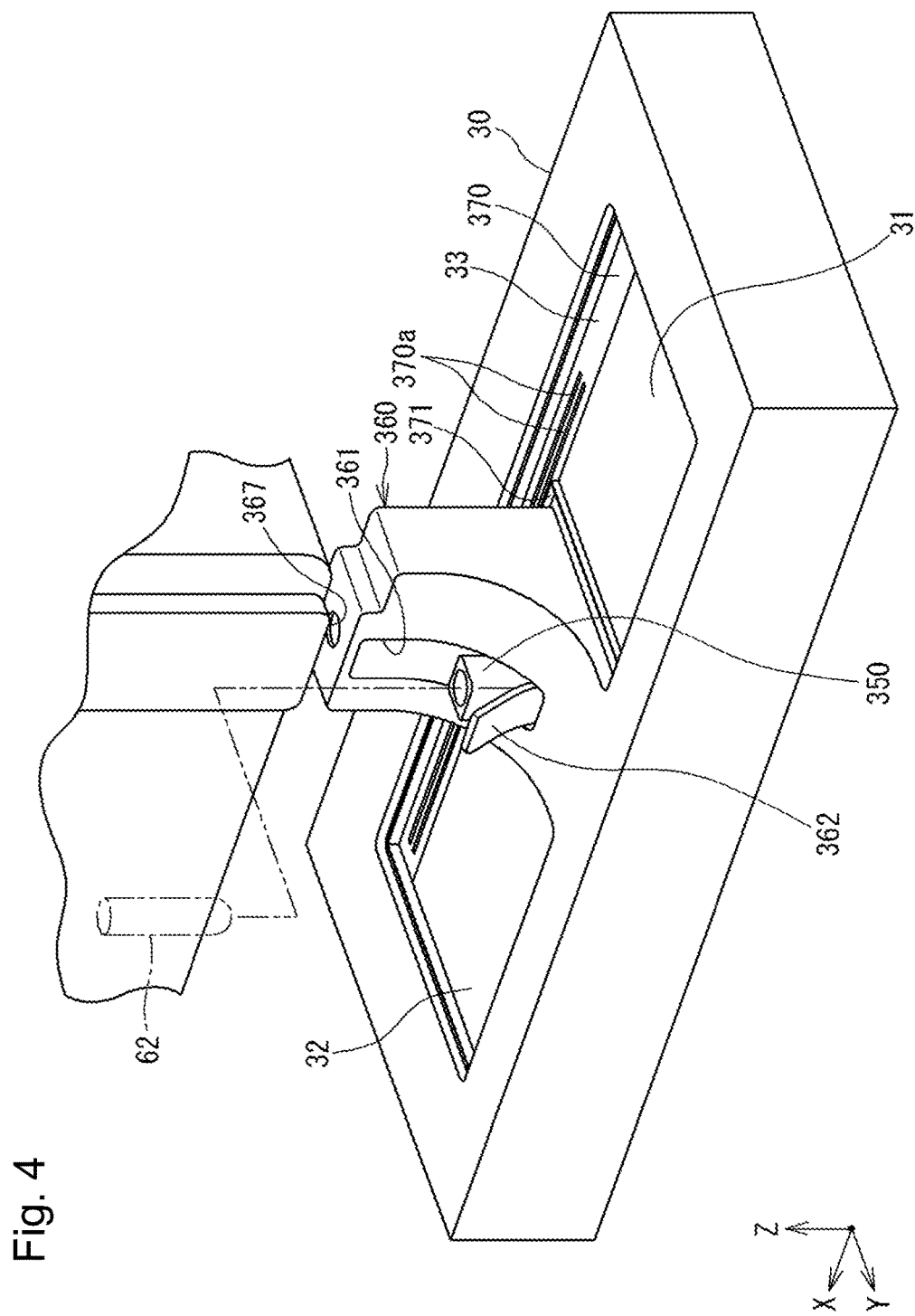
FIG. 4 is a perspective view of a transportation apparatus.

As illustrated in FIG. 4, transport part 30 has setting part 350 in which is set second sample container 62. Setting part 350 is formed in a bottomed cylindrical shape with the upper part opened, and holds one second sample container 62 inserted from the upper opening. Setting part 350 is disposed between first placement region 31 and second placement region 32, in front of transport part 33.

Figure 5:
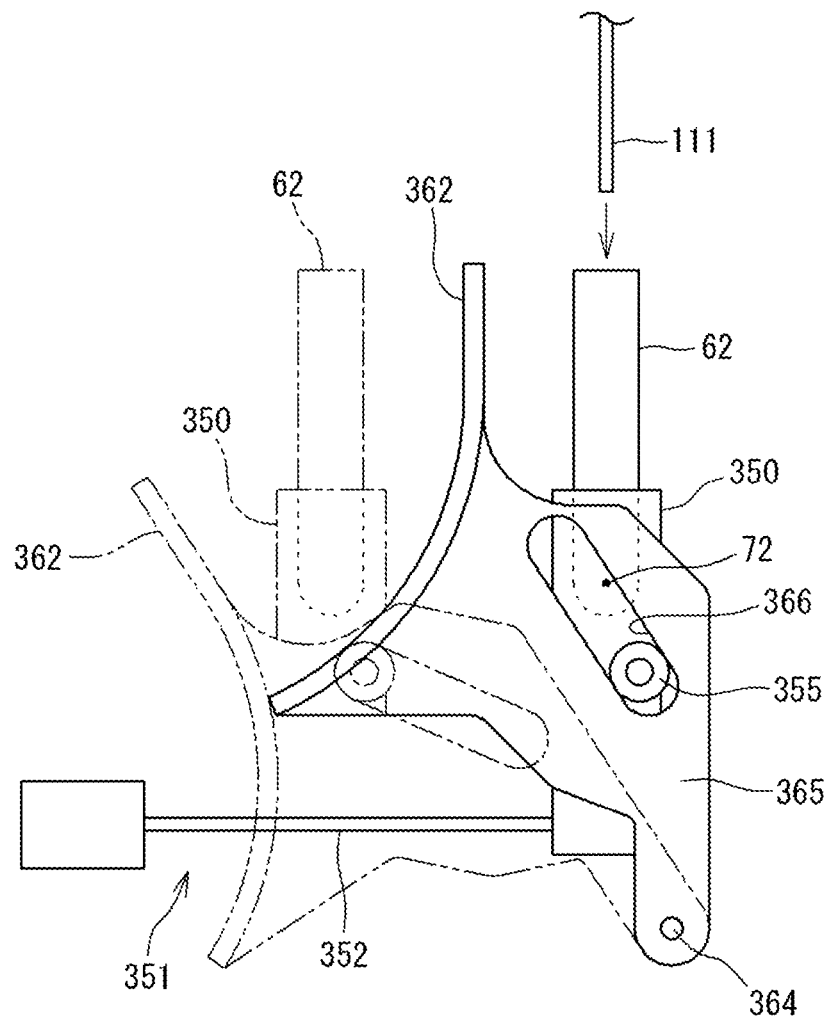
FIG. 5 is a view of the operation mechanism of a cover and a setting part.

As illustrated in FIG. 5, setting part 350 can move in the Y direction, which is the longitudinal direction. Setting part 350 is normally accommodated in storage part 360, provided between first placement region 31 and second placement region 32. Storage part 360 is disposed on the front side of transport part 33.

Storage part 360 has opening 361 formed in the front side and cover 362 that opens and closes opening 361. When cover 362 opens, setting part 350 moves forward and is outside storage part 360. Second sample container 62 can be set in setting part 350 outside storage part 360.

Within storage part 360 is provided driving unit 351, which moves setting part 350 forward and backward. Driving unit 351 is configured using, for example, a rod cylinder. Driving unit 351 has rod 352 a tip of which is attached to setting part 350, and can move rod 352 forward and backward. By moving rod 352 forward and backward, driving unit 351 can move setting part 350 forward and backward. Driving unit 351 is controlled by controller 40.

Cover 362 is provided to enable swinging about support shaft 364, which is provided within storage part 360. Support shaft 364 is oriented with the shaft direction in the X direction. Cover 362 has linking piece 365 that links the rear part of cover 362 and support shaft 364. The rear end of linking piece 365 is swingably attached to support shaft 364. In FIG. 5, cover 362 is opened by swinging counterclockwise about support shaft 364, and is closed by swinging clockwise.

The opening/closing operation of cover 362 and the longitudinal movement of setting part 350 are coordinated. Setting part 350 has roller 355 midway in the vertical direction thereof. Roller 355 is rotatably and slideably inserted into long hole 366 formed in linking piece 365. When setting part 350 is moved forward by driving unit 351, roller 355 pushes linking piece 365 forward. As a result, cover 362 swings counterclockwise and opens.

When setting part 350 is moved backward by driving unit 351, setting part 350 is stored within storage part 360, and, in coordination therewith, cover 362 is closed. Through the backward movement of setting part 350, second sample container 62 set in setting part 350 is positioned at second sample aspiration position 72. The closing operation of cover 362 can also be performed by a manual operation by an operator. More specifically, when an operator pushes backward on cover 362, cover 362 is closed. When cover 362 is closed, in coordination therewith, setting part 350 moves backward and is stored within storage part 360.

Figure 6:
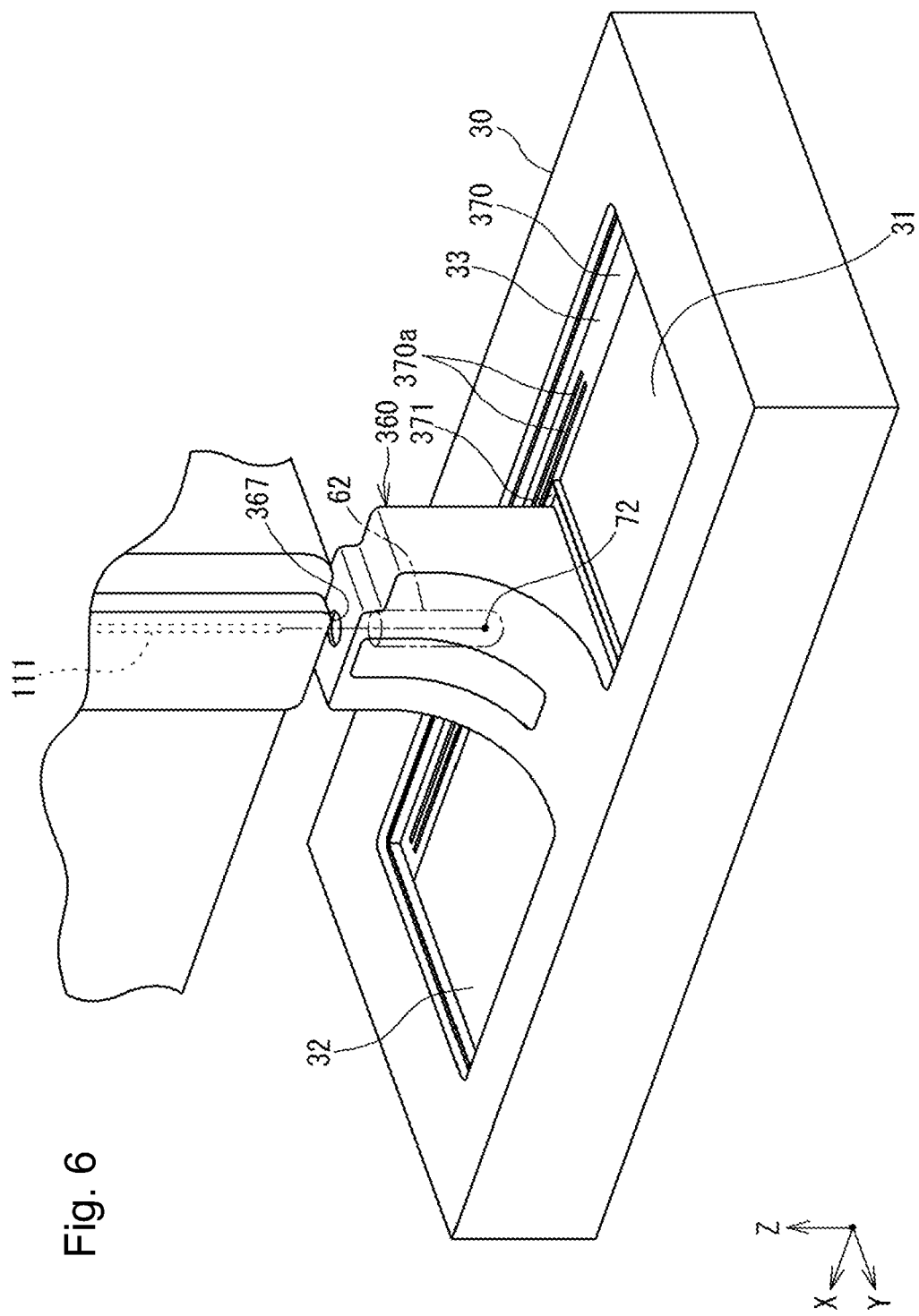
FIG. 6 is a perspective view of a transportation apparatus.

As illustrated in FIG. 4 and FIG. 6, opening 367 is present in the upper part of storage part 360. Opening 367 is provided for first nozzle 111 to advance into storage part 360 from above. As illustrated in FIG. 6, when second sample container 62 is set at second sample aspiration position 72, first nozzle 111 moves horizontally to a position above second sample aspiration position 72. Then, first nozzle 111 moves downward, advances into storage part 360 from opening 367, and aspirates the sample from second sample container 62.

Figure 7:
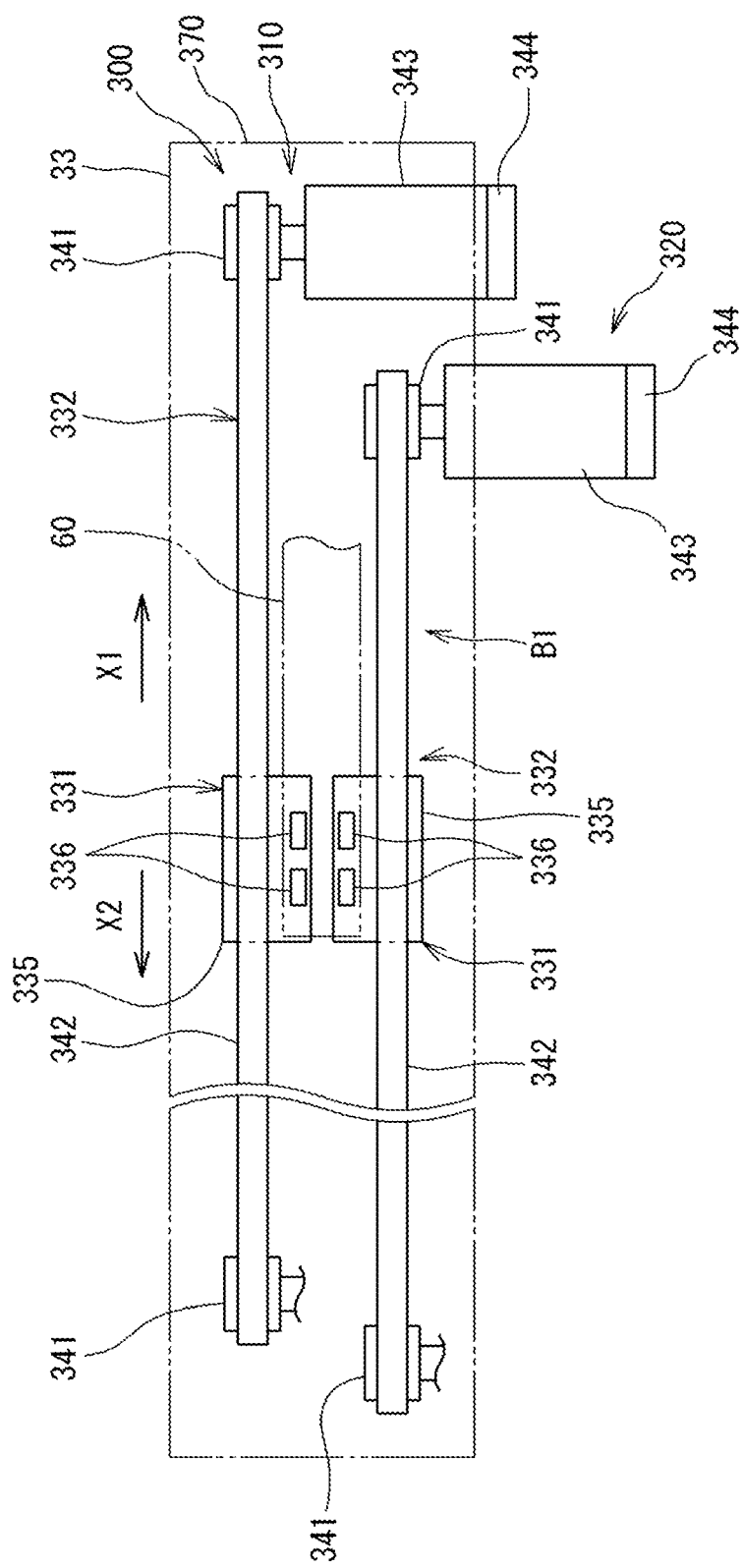
FIG. 7 is a plan view of a transportation apparatus.

FIG. 7 and FIG. 8 illustrate transport mechanism 300, which transports rack 60. Transport mechanism 300 is disposed below placement plate 370, which forms the transport pathway of transport part 33. Transport mechanism 300 comprises first mechanism 310 and second mechanism 320. First mechanism 310 and second mechanism 320 can each transport rack 60. More specifically, transport part 33 of the embodiment can transport two racks 60.

First mechanism 310 and second mechanism 320 each comprise engaging unit 331 that engages rack 60 and movement mechanism 332 that moves engaging unit 331 in the X direction, which is the right-left direction.

Each movement mechanism 332 comprises a pair of pulleys 341, endless belt 342 wound about pulleys 341, motor 343 that causes one pulley 341 to rotate, and rotary encoder 344 that detects the speed of motor 343. Motor 343 is, for example, a stepper motor.

Engaging units 331 are linked with endless belts 342, and move in the X1 direction and the X2 direction through rotation of motor 343. Through movement of engaging unit 331 engaged with rack 60, rack 60 moves along transport pathway of transport part 33. The amount of movement of engaging unit 331, and more specifically, the amount of movement of rack 60, is calculated using the number of driving pulses imparted to motor 343 by controller 40. The speed of motor 343 may be detected by rotary encoder 344 provided in motor 343. The position of rack 60 in transport part 33 is calculated assuming rack acceptance position 33a is the initial rack position, and based on the initial rack position and the rack movement amount. Acceptance of rack 60 at rack acceptance position 33a is detected by rack detector 91 provided in transport part 33 (see FIG. 1). Rack detector 91 is, for example, a photointerruptor. When rack 60 is detected by rack detector 91, controller 40 recognizes that rack 60 is positioned at rack acceptance position 33a, that is, and the initial rack position.

Engaging unit 331 comprises base 335 attached to endless belt 342 and engaging protuberances 336 provided on base 335. Engaging protuberances 336 engage recessed wall 65 formed in the bottom part of rack 60. By engaging protuberances 336 engaging in recessed wall 65, whereby engaging unit 331 is fastened to rack 60. Engaging protuberances 336 engage the bottom part of rack 60 on placement plate 370 through grooves 370a formed in placement plate 370 of transport part 33. Grooves 370a are elongated along the X direction, which is the transport pathway direction of transport part 33. Two grooves 370a are provided arranged in parallel in the longitudinal direction. Engaging protuberances 336 of first mechanism 310 can protrude upward from one groove 370a, and engaging protuberances 336 of second mechanism 320 can protrude upward from another groove 370a.

Because transport mechanism 300 comprises first mechanism 310 and second mechanism 320, two racks 60A, 60B placed on transport part 33 can be moved, as illustrated in FIG. 8.

4. Control

Figure 9:
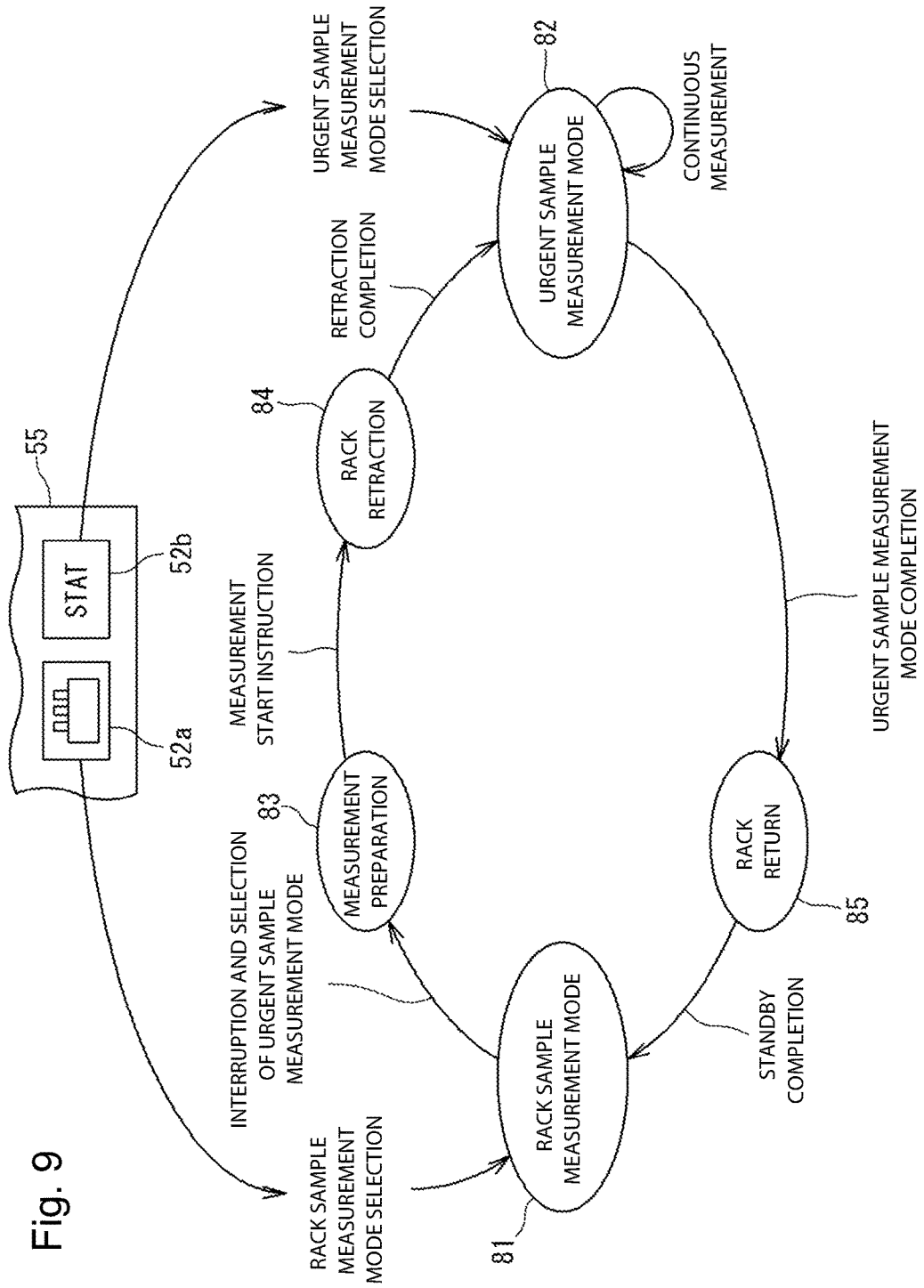
FIG. 9 is a state transition diagram showing states of processing execution performed by a controller.

There are two measurement modes in the sample measurements performed by controller 40. As illustrated in FIG. 9, the first measurement mode is rack sample measurement mode 81, and the second measurement mode is urgent sample measurement mode 82. In rack sample measurement mode 81, samples in first sample containers 61 held in rack 60 are measured continuously. For continuous measurements, first sample containers 61 are sequentially transported to first sample aspiration position 71. In urgent sample measurement mode 82, a sample in second sample container 62 set in setting part 350 is measured.

Modes 81, 82 are executed by selecting selection buttons 52a, 52b displayed on display screen 55 of display 52. First selection button 52a is used for selection of rack sample measurement mode 81. Second selection button 52b is used for selection of urgent sample measurement mode 82. First selection button 52a is a first instruction part that receives an instruction for measurement of samples in first sample containers 61. Second selection button 52b is a second instruction part that receives an instruction for measurement of a sample in second sample container 62. When selection buttons 52a, 52b are selected by operation of input unit 53, respective modes 81, 82 are executed.

Figure 10:
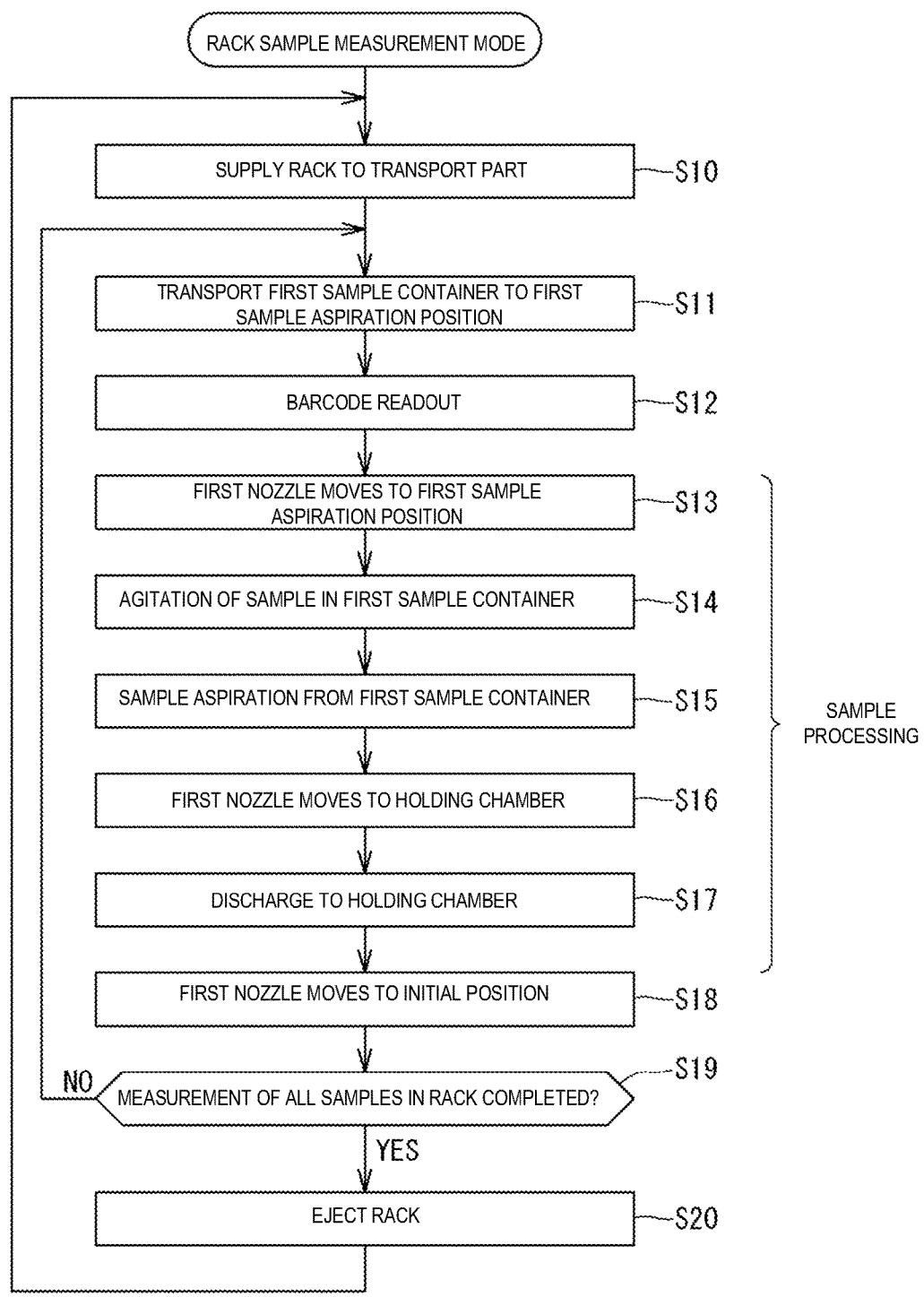
FIG. 10 is a flowchart of a rack sample measurement mode.

When first selection button 52a is selected, controller 40 executes processing for the track sample measurement mode illustrated in FIG. 10. First, in step S10, rack 60 placed in first placement region 31 moves in the Y2 direction, and is supplied to rack acceptance position 33a of transport part 33. Acceptance of rack 60 at rack acceptance position 33a is detected by rack detector 91 provided in transport part 33. Through step S10, controller 40 recognizes that rack 60 has been positioned on the transport pathway by transport part 33. When racks 60 are placed in first placement region 31, two racks 60 are supplied to transport part 33. In step S11, among first sample containers 61 held in rack 60, first sample container 61 at the left end of rack 60, and more specifically at the end on the second placement region 32 side, is transported to first sample aspiration position 71 by transport part 33. In step S12, readout unit 90 reads out barcode 67 on first sample container 61 that has been transported to first sample aspiration position 71, which is also an information readout position. Through readout of barcode 67, the sample number and other sample information is read out.

Next, in step S13, first nozzle 111 is moved from initial position 73 to first sample aspiration position 71 by first driving unit 112. In step S14, first nozzle 111, positioned at first sample aspiration position 71, agitates the sample within first sample container 61. Sample agitation is performed by having agitation nozzle 111c of first nozzle 111 aspirate the sample from first sample container 61, and again discharge the aspirated sample. Sample aspiration and discharge by agitation nozzle 111c is performed multiple times.

In step S15 following sample agitation, aspiration nozzle 111b of first nozzle 111 aspirates the agitated sample from first sample container 61. In step S16, first nozzle 111, having aspirated the sample, moves to discharging position 74. In step S17, first nozzle 111 discharges the aspirated sample to holding chamber 220, which is provided in discharging position 74. In step S18, first nozzle 111 is cleaned in preparation for the next sample aspiration, and moves to initial position 73, which is a standby position.

In step S19, a determination is made as to whether measurement of the samples of all first sample containers 61 held in rack 60 on transport part 33 has been completed. If measurement of the samples of all first sample containers 61 held in rack 60 is not completed, step 11 to step S18 are performed again in order to continue sample measurement. More specifically, first sample container 61 from which a sample is to be aspirated next is transported to first sample aspiration position 71, and then sample agitation, sample aspiration, sample discharging, and the like are performed. If measurement of the samples of all first sample containers 61 held in rack 60 is completed, in step S20 rack 60 is transported to rack ejection position 33b by transport part 33, and is ejected to second placement region 32. Through step S20, controller 40 recognizes that rack 60 is no longer positioned over the transport part pathway of transport part 33. After ejecting rack 60 to second placement region 32, if another rack 60 is placed in first placement region 32, processing returns to step S10, and rack 60 in first placement region 32 is supplied to transport part 33.

Samples discharged to holding chamber 220 are dispensed to processing chambers 231, 232 by second unit 120. In processing chambers 231, 232, measurement specimens are prepared, and measurement specimens are sent to detector 260. Detection unit 260 detects components of samples prepared as measurement specimens. In this embodiment, dispensing of samples from first sample containers 61 to processing chambers 231, 232 is performed separately by first unit 110 and second unit 120, and therefore operations of first unit 110 and operations of second unit 120, and subsequent operations, can be performed in parallel. For example, while dispensing certain samples to processing chambers 231, 232, preparing measurement specimens, and performing component detection, the next sample can be aspirated by first nozzle 111. In other words, first nozzle 111 can aspirate the next sample before completion of measurement specimen preparation in processing chambers 231, 232.

As shall be apparent, selection of second selection button 52b can be performed when rack sample measurement mode 81 is not being executed, and can also be performed during execution of rack sample measurement mode 81. More specifically, second selection button 52b can be selected at a desired time in the measurement procedure illustrated in FIG. 10. When interrupting execution of rack sample measurement mode 81 to execute urgent sample measurement mode 82, transport of rack 60 by transport part 33 is interrupted, and measurement of the urgent sample in the second sample container set in setting part 350 is performed.

By selecting second selection button 52b to issue an instruction for urgent sample measurement, the need for aspiration of the urgent sample arises. In place of second selection button 52b displayed on a screen, an instruction part that receives instructions for measurement of urgent samples may also be a mechanical button that can perform a physical pushing operation. A configuration is also possible in which, when setting of second sample container 62 in setting part 350 has been detected, an instruction for measurement of the urgent sample is received. A configuration is also possible in which, when it is detected that cover 362 is closed, setting of second sample container 62 in setting part 350 is detected.

Figure 11:
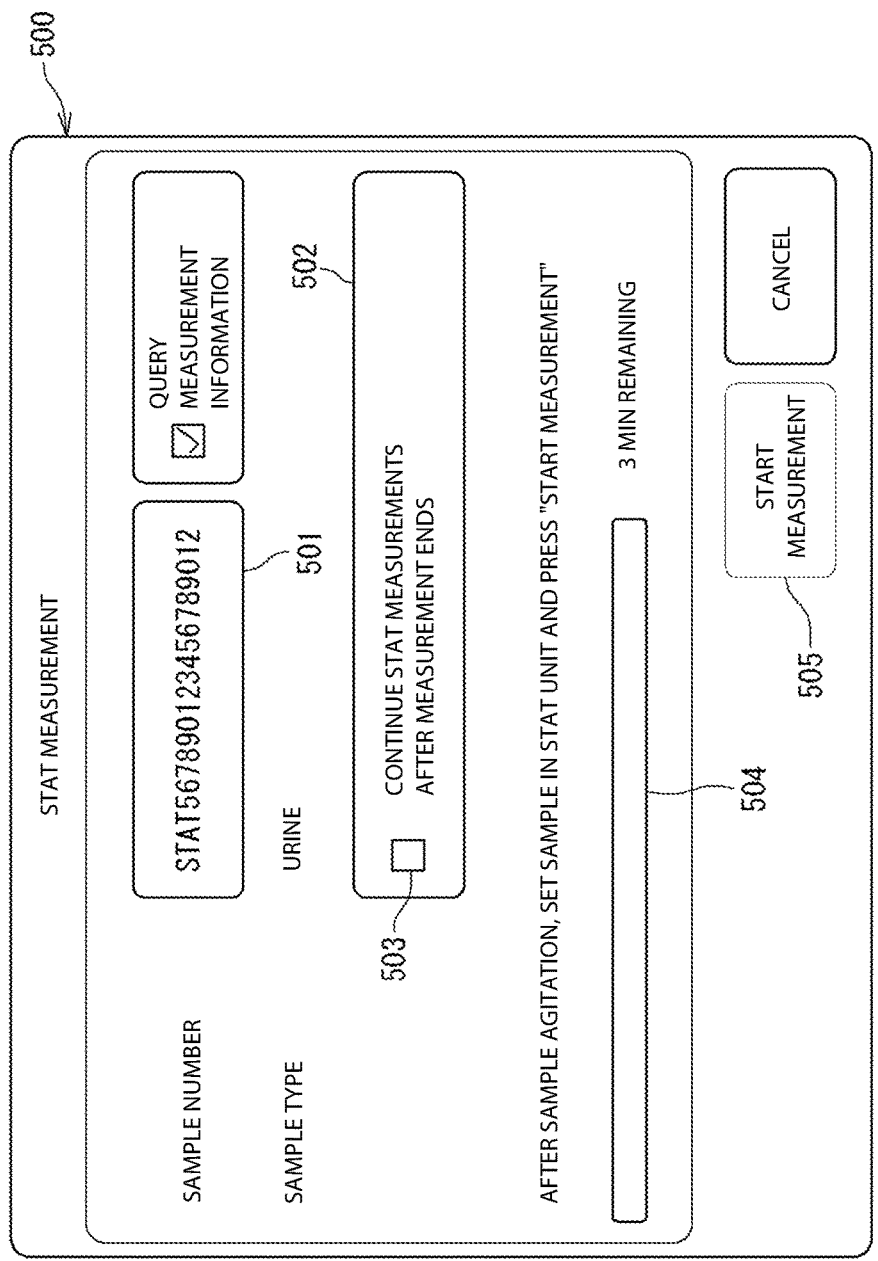
FIG. 11 is a drawing illustrating an urgent measurement diagram.

When second selection button 52b is selected, urgent (STAT) measurement dialog 500 illustrated in FIG. 11 is displayed, and measurement preparation processing 83 illustrated in FIG. 9 is executed. Urgent measurement dialog 500 includes sample number input region 501, continuous measurement setting region 502, progress bar 504, measurement start button 505, and the like. Sample number input region 501 is a region for input by an operator of the sample number of the urgent sample. Continuous measurement setting region 502 is a region for setting whether or not to perform continuous measurements of urgent samples. When the operator checks the checkbox 503 included in continuous measurement setting region 502, measurement of other urgent samples is continued after the end of measurement of an urgent sample. Progress bar 504 indicates the time until completion of measurement preparation processing 83. Measurement start button 505 is a button to instruct that measurement of the urgent sample be started.

Measurement preparation processing 83 is performed when second selection button 52b is selected, and the need has arisen for aspiration of an urgent sample by first nozzle 111. Measurement preparation processing 83 is executed prior to the start of urgent sample measurement mode 82. The measurement preparation processing is indicated in step S21 to step S28 in FIG. 12. In measurement preparation processing 83, first urgent measurement dialog 500 is displayed in step S21. In step S22, controller 40 determines whether or not first sample container 61 is being transported to first sample aspiration position 71. More specifically, in step S22, it is determined whether second selection button 52b was selected and the need for aspiration of an urgent sample arose during step S11.

In step S22, when it is determined that step S11 is not being executed and that rack 60 is in a stopped state, and more specifically, when rack 60 is stopped at rack acceptance position 33a, or when rack 60 is stopped above first sample aspiration position 71, in step S24 the current position of rack 60 is stored in storage apparatus 42 of controller 40. The current position of rack 60 is the position of rack 60 in transport part 30 at the time when transport of rack 60 was interrupted.

In step S22, when it is determined that step S11 is being executed and that rack 60 is in a movement state, step S23 is performed. In step S23, instead of interrupting movement of rack 60 midway, after first sample container 61 from which sample aspiration is next to be performed arrives at first sample aspiration position 71, transport of rack 60 in rack sample measurement mode 81 is interrupted. That is, when second selection button 52b is selected during step S11, after step S11 is completed, rack sample measurement mode 81 is interrupted.

Next, when first sample container 61, in which the sample is to be aspirated, arrives at first sample aspiration position 71, the current position of the rack is stored, as in step S24. The current rack position stored in step S24 is used for returning rack 60 when returning from urgent sample measurement mode 82 to rack sample measurement mode 81. Even when urgent sample measurement mode 82 is selected during movement of rack 60, movement of rack 60 is continued until first sample container 61 that is to aspirate a sample next arrives at first sample aspiration position 71, and therefore rack 60 is easily returned.

In step S25, controller 40 determines whether sample processing is being performed for first sample container 61 at first aspiration position 71. In this embodiment, sample processing for first sample container 61 is processing from step S13 to step S18 in FIG. 10. More specifically, sample processing is the processing performed from when first nozzle 111 begins movement from initial position 73 until being returned to initial position 73. When second selection button 52b is selected during sample processing, sample processing is not interrupted immediately, but rack sample measurement mode 81 is interrupted after completion of the sample processing currently being performed. As a result, there is no longer a need to re-perform from the start the sample processing for first sample container 61 currently being performed. Further, when second selection button 52b is selected during sample processing subsequent to step S13, instead of continuing processing up to step S18, rack sample measurement mode 81 may be interrupted after completion of processing up to detection of sample components by detector 260.

In step S27, controller 40 stores the state of progress of processing in the rack sample measurement mode in storage apparatus 42. The stored state of processing progress is used to continue processing in rack sample measurement mode 81 after returning from urgent sample measurement mode 82 to rack sample measurement mode 81.

Types of processing progress states that are stored include three states; i.e., a first state, a second state, and a third state. The first state is the state in which first sample container 61, which is to aspirate a sample, has been transported to first sample aspiration position 71, but readout of the barcode of first sample container 61 has not been performed, and is the state from step S11 to step S12 in FIG. 1. The second state is the state in which barcode readout for first sample container 61 has been performed, but sample processing (from step S13 to step S18) for first sample container 61 has not been performed, and is the state from step S12 to step S13 in FIG. 10. The third state is the state in which sample processing has been completed and first sample container 61 that is to aspirate a sample next has not yet arrived at first sample aspiration position 71, and is the state from step S18 to step S11, which is performed next after step S18, in FIG. 10. When returning from urgent sample measurement mode 82 to rack sample measurement mode 81, controller 40 essentially returns to the state indicated by the stored processing progress state.

In this embodiment, urgent sample measurement mode 82 can be selected at a desired time during execution of rack sample measurement mode 81 illustrated in FIG. 10. However, even when urgent sample measurement mode 82 is selected, instead of rack sample measurement mode 81 being immediately interrupted, execution is performed until when it is convenient to stop, as in the first through third states, whereupon rack sample measurement mode 81 is interrupted. Consequently, return to rack sample measurement mode 81 is facilitated.

The state of progress of processing from step S22 to step S27 is indicated by progress bar 504. When processing up to step S27 is completed, progress bar 504 disappears from urgent measurement dialog 500. When a sample number has been inputted into sample number input region 504 of urgent measurement dialog 500, measurement start button 505 becomes active, as indicated in step S28, and measurement start button 505 can be selected. In step S28, cover 362 opens and second sample container 62 can be set in setting part 350, as illustrated in FIG. 4. Thus when second selection button 52b is selected, cover 362 opens automatically. Cover 362 may also be configured so as to be opened manually when second selection button 52b has not been selected.

When the operator sets second sample container 62 in setting part 350 and selects measurement start button 505 to issue a measurement start instruction, rack retraction processing 84 (see FIG. 9), indicated in step S29, is performed. In step S30, urgent measurement dialog 500 is closed. Thereafter, second sample container 62 set in setting part 350 moves to second sample aspiration position 72, cover 362 is closed, and execution of urgent measurement mode 82 is started.

After retraction processing 84 of rack 60, urgent sample measurement mode 82 is executed. After the completion of execution of urgent sample measurement mode 82, return processing 85 is performed for rack 50, and execution of rack sample measurement mode 81 is resumed. Retraction processing 84 and return processing 85 are described below.

Figure 13:
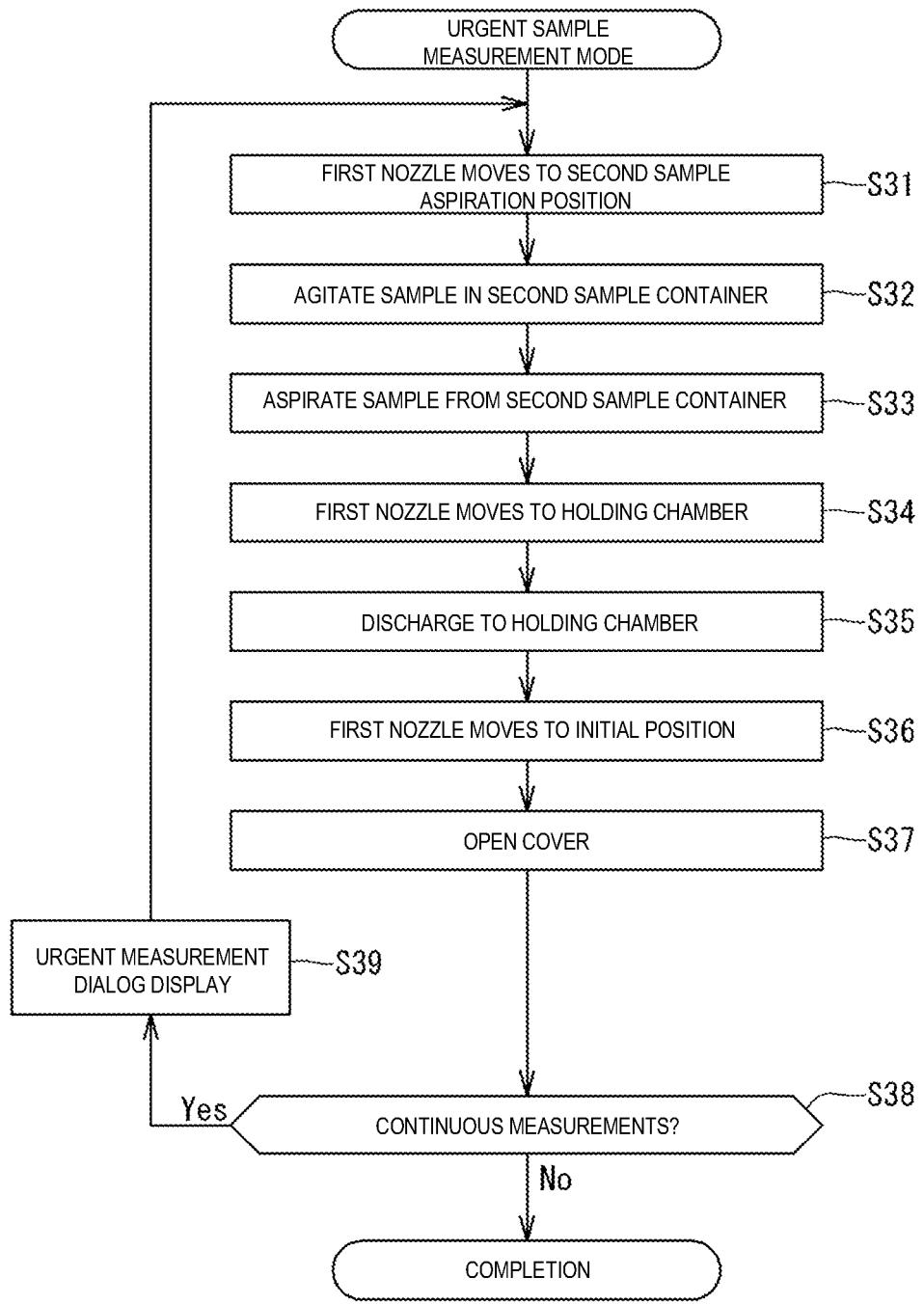
FIG. 13 is a flowchart of an urgent sample measurement mode.

In urgent sample measurement mode 82, controller 40 executes the processing indicated in FIG. 13. In step S31, first nozzle 111 is moved by first driving unit 112 from initial position 73 to second sample aspiration position 72. In step S32, first nozzle 111, which is positioned at second sample aspiration position 72, agitates the urgent sample within second sample container 62.

In step S33 after sample agitation, first nozzle 111 aspirates the agitated sample from second sample container 62. In step S34, first nozzle 111, which has aspirated the sample, moves to discharging position 74. In step S35, first nozzle 111 discharges the aspirated sample to holding chamber 220 provided at discharging position 74. In step S36, first nozzle 111 is cleaned in preparation for aspiration of the next sample, and moves to initial position 73, which is a standby position.

The sample that has been discharged to holding chamber 220 is dispensed to processing chambers 231, 232 by second unit 120. In processing chambers 231, 232, measurement specimens are prepared, and measurement specimens are sent to detector 260. Detection unit 260 detects the components of samples prepared as measurement specimens.

When first nozzle 111 returns to initial position 73, in step S37 cover 362 opens, and setting part 350 moves forward. As a result, second sample container 62, for which sample aspiration has ended, can be removed from setting part 350. In this embodiment, dispensing of the sample from second sample container 61 to processing chambers 231, 232 is performed separately by first unit 110 and second unit 120, and therefore the operation of first unit 110, the operation of second unit 120, and subsequent operations can be performed in parallel. Cover 362 may be opened after completion of the processing up to detection of sample components by detector 260.

In step S38, controller 40 determines whether or not continuous measurement of urgent samples has been set. In urgent measurement dialog 500 of FIG. 11, when checkbox 503 for continuous measurement of urgent samples has been checked, that is, when continuous measurement of urgent samples has been set, processing proceeds to step S39 and urgent measurement dialog 500 is displayed. The operator sets the next second sample container 62 in setting part 350, inputs the sample number, and selects measurement start button 505, whereupon urgent measurement dialog 500 is closed, and processing of step S31 and beyond is again repeated.

Figure 14:
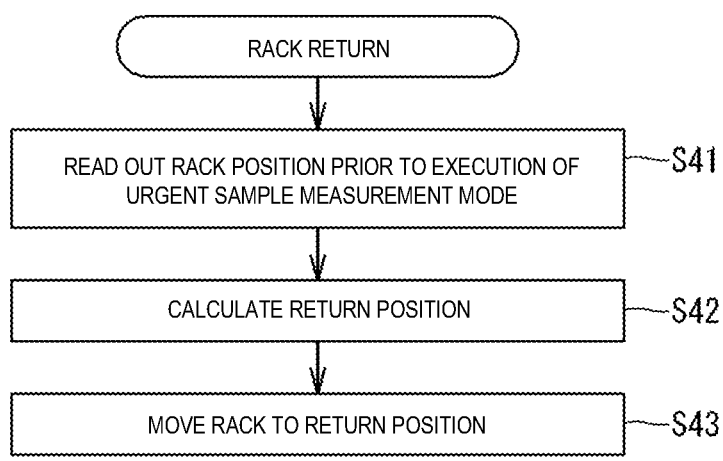
FIG. 14 is a flowchart of rack return processing.

When continuous measurement of urgent samples has not been set, urgent measurement mode 82 is completed, and after return processing 85 indicated in FIG. 14, processing returns to rack sample measurement mode 81. In rack sample measurement mode 81 to which processing has returned, the operation prior to interruption by urgent measurement mode 82 is continued, based on the processing progress state that has been stored. Rack return processing 85 is described below.

5. Rack Retraction and Return

Figure 15A:
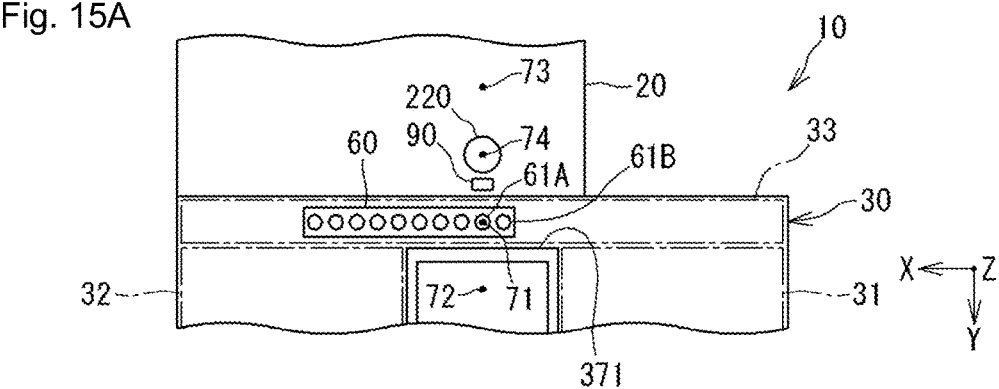
FIGS. 15A, 15B, 15C, and 15D are views illustrating rack retraction and return.

FIGS. 15A to 15D, 16A, 16B, 17A to 17C, 18A and 18B illustrate the manner of movement of first sample container 61 due to retraction and return of rack 60. In FIG. 15A, one rack 60 is placed on transport part 33, and the second first sample container 61A from the right in rack 60 is positioned at first sample aspiration position 71. In the state of FIG. 15A, it shall be assumed that second selection button 52b is selected and the need arises to aspirate an urgent sample using first nozzle 111. Further, it shall be assumed that second selection button 52b is selected midway in processing from step S13 to step S18 in FIG. 10. When second selection button 52b is selected, after processing up to step S18 is completed, a transition is made to urgent sample measurement mode 82. In this case, controller 40 stores the position indicated in FIG. 15A as the current position of rack 60. Further, as the processing progress state, controller 40 stores the state in which sample processing for first sample container 61A at first sample aspiration position 71 has been completed, but first sample container 61B to which the next sample is to be aspirated has not arrived at first sample aspiration position 71. This state is the above-described third state.

Figure 15B:
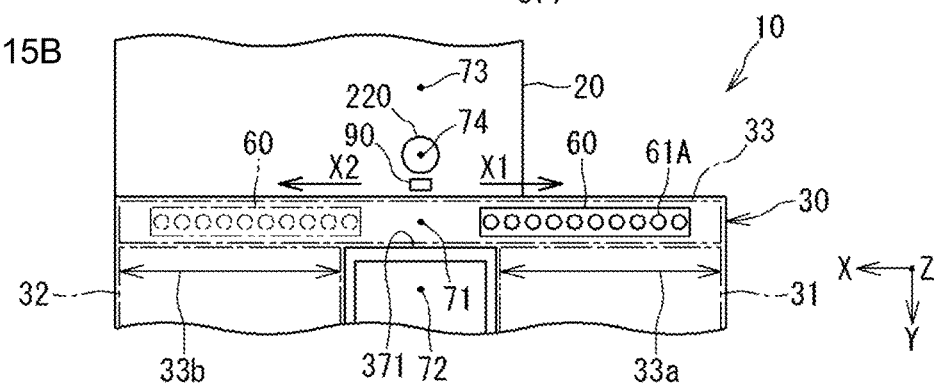
Figure 15C:
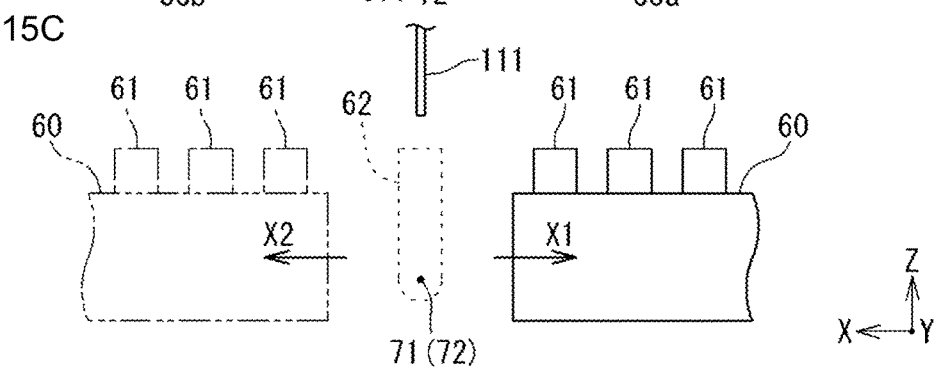

In this case, when rack retraction processing 84 is performed, rack is moved along the transport pathway by transport part 33 for retraction, and is retracted to the position illustrated in FIG. 15B and FIG. 15C. Rack 60, indicated by a solid line in FIG. 15B and FIG. 15C, illustrates the retraction position after having moved in the X1 direction toward rack acceptance position 33a for retraction. In FIG. 15B and FIG. 15C, rack 60, indicated by a dot-dot-dash line, illustrates the retraction position after having moved in the X direction toward rack ejection position 33b for retraction. Thus, the retraction position may be rack acceptance position 33a, or may be rack ejection position 33b.

In FIG. 15B and FIG. 15C, the entirety of rack 60 moves away from first sample aspiration position 71. In urgent sample measurement mode 82, in the states of FIG. 15B and FIG. 15C, first nozzle 111, which has aspirated an urgent sample from second sample container 62 at second sample aspiration position 72, moves above first sample aspiration position 71 toward holding chamber 220. First sample containers 61 are not present below transport pathway 75 of first nozzle 111. That is, first sample containers 61 are positioned at a distance from directly below transport pathway 75 of first nozzle 111. Hence even if a sample were to fall from first nozzle 111, contamination of the sample in first sample containers 61 would be prevented. In this embodiment, before aspiration of an urgent sample, first nozzle 1 agitates the urgent sample, and consequently the sample adheres readily to the outer periphery of first nozzle 111, and the possibility of falling of the sample from the outer periphery of first nozzle 111 is increased, but even if falling of the sample occurs, contamination of first sample containers 61 is reliably prevented.

The retraction position of rack 60 may be a position coinciding with rack acceptance position 33a or with rack ejection position 33b, but in this embodiment, the retraction position of rack 60 is set at a position closer to first sample aspiration position 71 than rack acceptance position 33a or rack ejection position 33b. When rack 60 is retracted to rack acceptance position 33a or to rack ejection position 33b, rack 60 can easily be removed from transport part 33, and there is the concern that the operator may erroneously remove the retracted rack 60.

On the other hand, in this embodiment there is little concern that the operator may erroneously remove the retracted rack 60. That is, as illustrated in FIG. 4, regulating part 371 is provided in transport part 33. Regulating part 371 regulates forward movement of rack 60 between rack acceptance position 33a and rack ejection position 33b. Regulating part 371 is configured as a wall that is erected on the front side of placement plate 370. Hence, as illustrated in FIG. 15B, by positioning at least a portion in the length direction of rack 60 within the range over which regulating part 371 is provided, concerns that the operator may erroneously remove rack 60 are reduced. Further, storage part 360 is erected between rack acceptance position 33a and rack ejection position 33b; therefore, in this respect also, concerns that the operator may erroneously remove rack 60 are reduced.

Figure 15D:
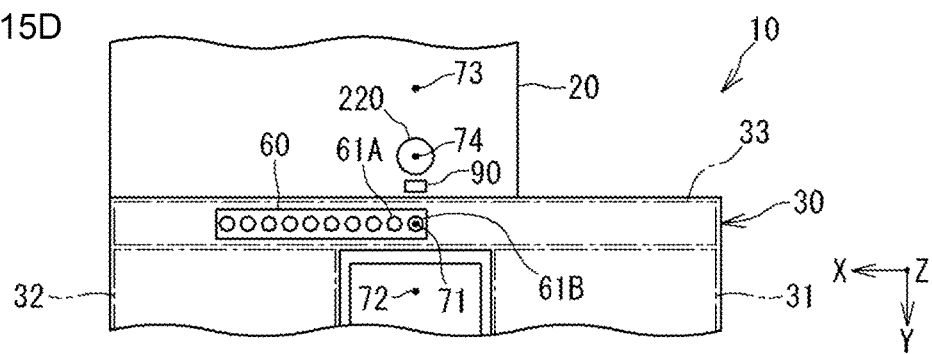

When urgent sample measurement mode 82 ends, that is, when, in a state in which continuous measurement of urgent samples has not been set the return of first nozzle 111 to initial position 73 is detected, controller 40 returns rack 60 by rack return processing 85, as illustrated in FIG. 15D. Moreover, rack return processing 85 may be started when first nozzle 111, which has aspirated an urgent sample, is detected as having passed above first sample aspiration position 71, or rack return processing 85 may be started when first nozzle 111, which has aspirated an urgent sample, is detected as having arrived at holding chamber 220. As indicated in FIG. 14, in rack return processing 85, the rack position before execution of urgent sample measurement mode 82 is read out in step S41. The read-out rack position is the current position of rack 60 stored by controller 40 in step S24 of FIG. 12. In step S42, the return position of rack 60 is calculated based on the read-out rack position. In step S43, rack 60 moves to the return position. In FIG. 15D, the return position is the position of the rack 60 that can position, at first sample aspiration position 71, first sample container 61B, which is to aspirate a sample next after first sample container 61A, which was at first sample aspiration position 71 at the time when an interrupt to rack sample measurement mode 81 has occurred. Specifically, storage apparatus 42 stores in advance the distance between the center points of the two adjacent container holding holes that hold first sample container 61A and first sample container 61B in rack 60. Controller 40 calculates the return position based on the rack position read out in step S41 and the distance between the center points.

Figure 12:
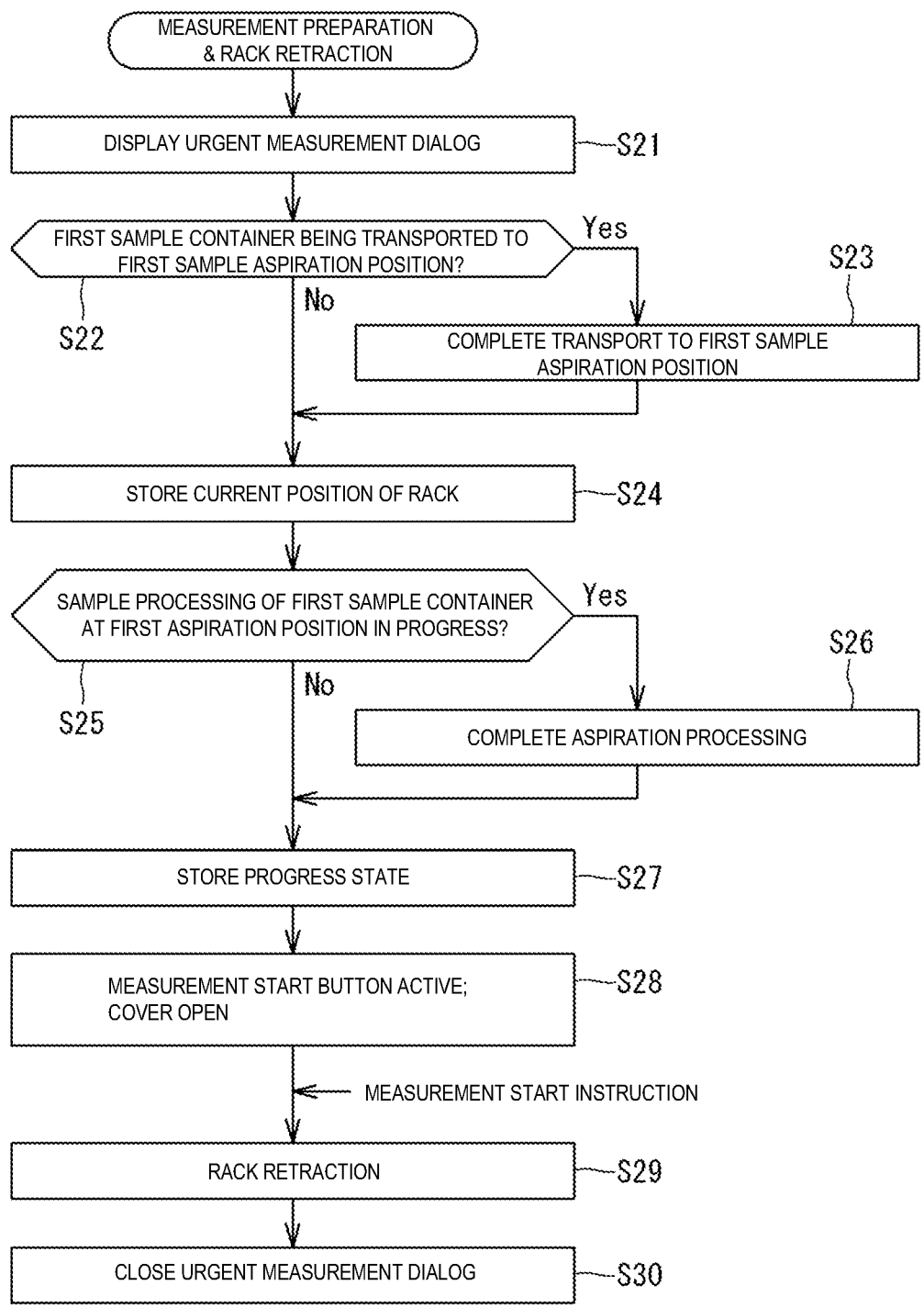
FIG. 12 is a flowchart of measurement preparation and rack retraction processing.

Rack 60 at the retraction position illustrated in FIG. 15B may simply be returned to the position of rack 60 illustrated in FIG. 15A based on the current position stored by controller 40 in step S24 of FIG. 12. However, in this case, first sample container 61A, which had been retracted, is returned to first sample aspiration position 71, after which step S11 in FIG. 10 is executed, and then first sample container 61B which is to aspirate the next sample must be transported to first sample aspiration position 71.

Conversely, in this embodiment, during rack return, first sample container 61B which is to aspirate the next sample, among first sample containers, is positioned at first sample aspiration position 71, as illustrated in FIG. 15D. Therefore, immediately after having returned to rack sample measurement mode 81, step S11 in FIG. 10 can be omitted. Further, in this embodiment, first sample aspiration position 71 is also a position for readout of sample information, and therefore the return of rack 60 to the position illustrated in FIG. 15D also serves to position first sample container 61B, from which sample information is to be read out next, at the information readout position.

Figure 16A:
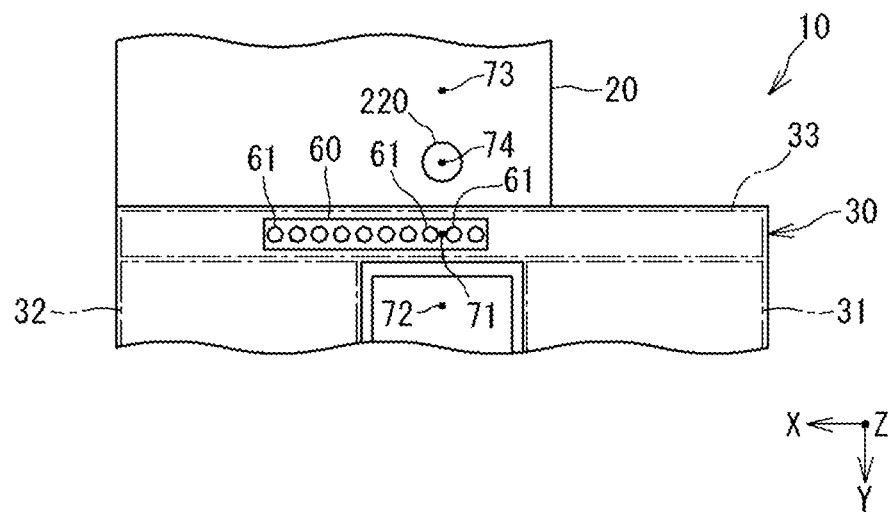
FIGS. 16A and 16B are views illustrating rack retraction.
Figure 16B:
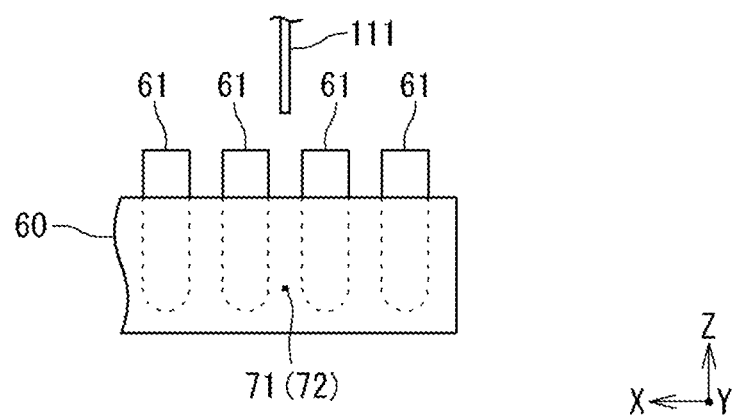

FIGS. 16A and 16B illustrate a modification of the retraction position of rack 60. In FIGS. 15A to 15D, the entirety of rack 60 had been retracted to a position distant from first sample aspiration position 71; in FIG. 16A and FIG. 16B, the rack is at first sample aspiration position 71, but first sample containers 61 held by rack 60 are at a position distant from first sample aspiration position 71. More specifically, in FIG. 16A and FIG. 16B, first sample containers 61 are retracted such that first sample aspiration position 71 is positioned between two adjacent first sample containers 61 held in rack 60. In this case, even if first nozzle 111, which has aspirated an urgent sample from second sample container 62, moves above first sample aspiration position 71, no first sample container 61 is present below transport pathway 75 of first nozzle 111, and therefore contamination with a sample in first sample container 61 is prevented. When retracting rack 60 as in FIGS. 16A and 16B, the amount of movement of rack 60 for retraction can be reduced.

Figure 17A:
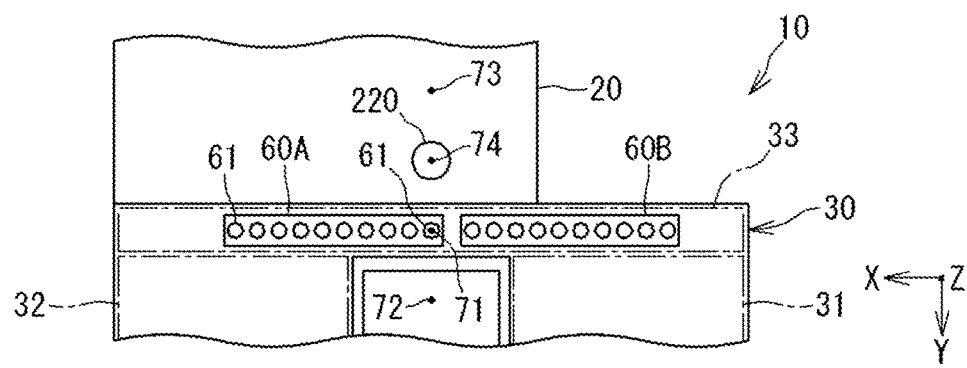
FIGS. 17A, 17B, and 17C are views illustrating rack retraction.
Figure 17B:
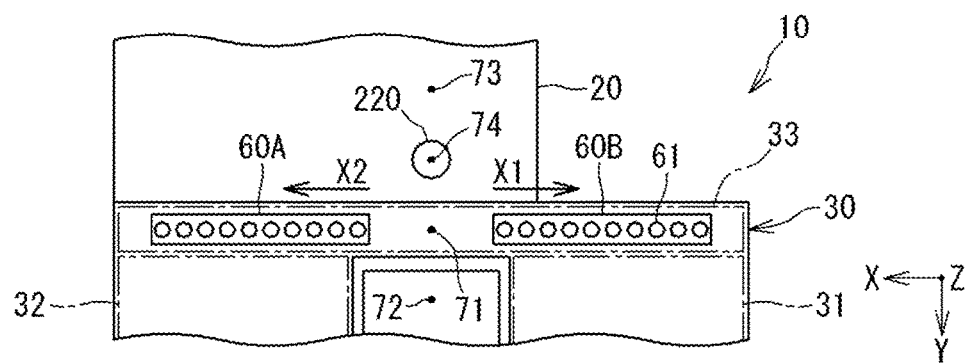
Figure 17C:
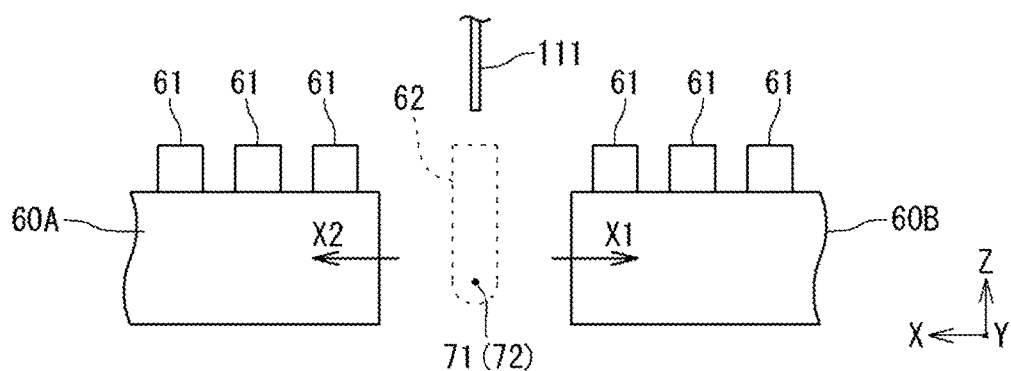

FIGS. 17A to 17C illustrate a method of retraction of rack 60 when two racks 60 are placed on transport part 33. In FIG. 17A, first rack 60A and second rack 60B are placed on transport part 33. First sample container 61 held in first rack 60A is at first sample aspiration position 71. In this case, when rack retraction processing 84 is performed, first rack 60A on the side of rack ejection position 33b moves to the retraction position on the side of rack ejection position 33b, and second rack 60B on the side of rack acceptance position 33a moves to the retraction position on the side of rack acceptance position 33a. That is, racks 60A and 60B move so as to be mutually distant on either side of first sample aspiration position 71. As a result, even when first nozzle 111, which has aspirated an urgent sample from second sample container 62, moves above first sample aspiration position 71, neither of racks 60A, 60B is present below the movement pathway 75 of first nozzle 111.

A case where two racks 60 are placed on transport part 33 is similar to the case illustrated in FIGS. 15A to 15D in any respects not explained in particular.

Figure 18A:
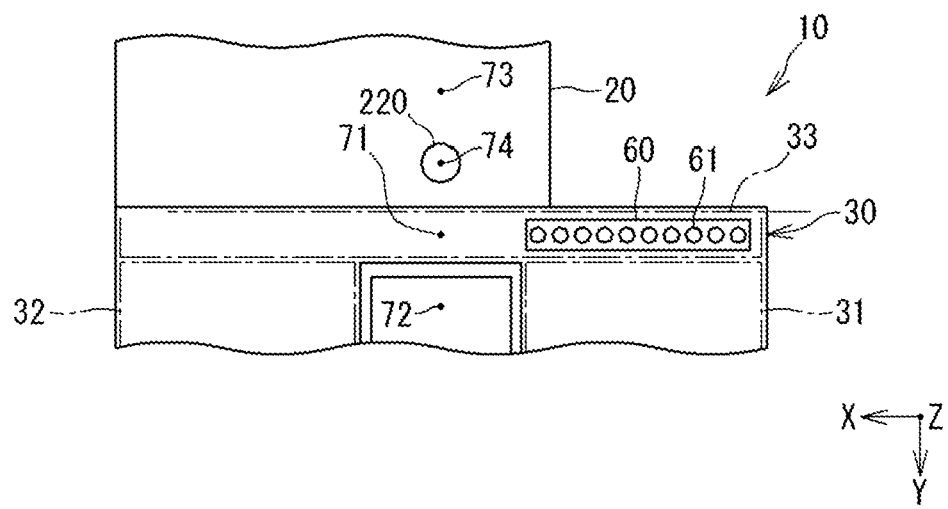
FIGS. 18A and 18B are views illustrating rack retraction.
Figure 18B:
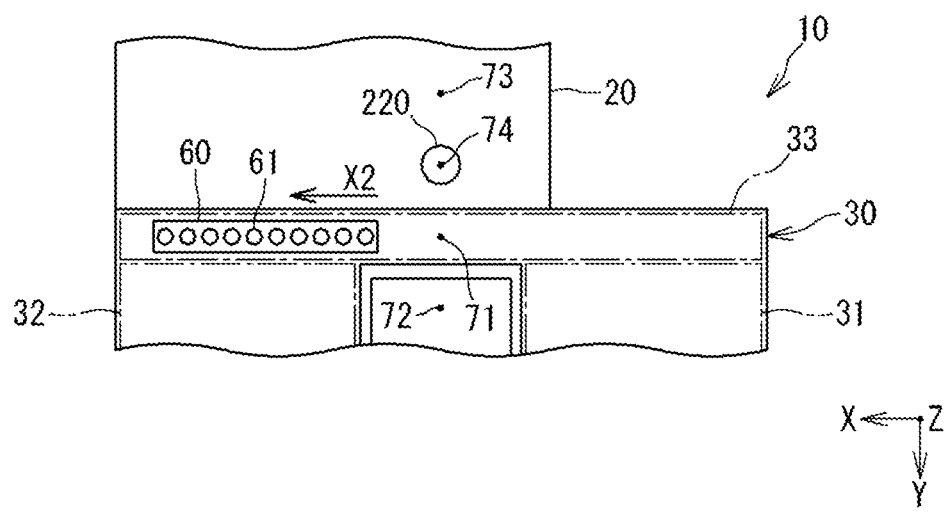

FIG. 18A and FIG. 18B illustrate retraction of rack 60 when one rack 60 is placed on transport part 33, but none of first sample containers 61 held in rack 60 is positioned at first sample aspiration position 71. In FIG. 18A, first sample containers 61 are not positioned at first sample aspiration position 71. The state illustrated in FIG. 18A is for example a state in which none of first sample containers 61 held in rack 60 has yet been transported to first sample aspiration position 71, and rack 60 is stopped at rack acceptance position 33a.

Suppose that, in the state of FIG. 18A, second selection button 52b is selected. In this case, no first sample container 61 is at first sample aspiration position 71, but in this case also controller 40 retracts rack 60, as illustrated in FIG. 18B. In this case, rack 60 moves to the side of rack ejection position 33b. Thus, in this embodiment, if rack 60 is on the transport pathway of transport part 33, even if not at first sample aspiration position 71, controller 40 retracts rack 60 to the previously set retraction position.

In the case of returning of retracted rack 60 to the position illustrated in FIG. 18B, rack 60 may be returned to the position illustrated in FIG. 18A, or may be positioned such that the first sample container 61 that is to aspirate the next sample among first sample containers 61 held in rack 60 is positioned at first sample aspiration position 71.

In the above-described embodiment, when second selection button 52b has been selected, regardless of whether a first sample container 61 is or is not positioned at first sample aspiration position 71, controller 40 moves rack 60 holding first sample containers 61 to a position distant from first sample aspiration position 71; but the invention is not limited to this embodiment. For example, when second selection button 52b has been selected, the controller 40 may determine whether a first sample container 61 is positioned at first sample aspiration position 71, and, when it is determined that a first sample container 61 is positioned at first sample aspiration position 71, may move rack 60 holding first sample container 61 to a position distant from first sample aspiration position 71, but when it is determined that no first sample container 61 is positioned at first sample aspiration position 71, rack 60 holding first sample containers 61 may be stopped at the current position without being moved.

In the above-described embodiment, a configuration is adopted in which transport part 33 transports rack 60 holding first sample containers 61. However, a configuration may be adopted in which transport part 33 does not transport rack 60; for example, a configuration may be adopted in which transport part 33 continuously transports container-holding parts capable of holding one first sample container 61.

Further, in the above-described embodiment, first nozzle 111 moves through positions higher than the upper end of rack 60 transported by transport part 33, or positions higher than first sample containers 61 held by rack 60. However, a configuration may be adopted in which first nozzle 111 moves through positions lower than the upper end of rack 60 transported by transport part 33, or lower than first sample containers 61 held by rack 60. By moving first nozzle 111 to lower positions, a sample that has dropped from first nozzle 111 can be prevented from going into first sample containers 61. Moreover, when first nozzle 111 moves after having aspirated a sample from second sample container 62, rack 60 has been retracted from movement pathway 75 of first nozzle 111 by rack retraction processing 84; therefore, contact of first nozzle 111 with rack 60 or with first sample containers 61 can be prevented.

In the above-described embodiment, an example was presented in which the invention is applied to sample analyzer 10 configured from one measurement unit 20 and one transportation apparatus 30, but the invention may also be applied to a sample analysis system configured from measurement units and transportation apparatuses provided corresponding to measurement units, as disclosed in Japanese Laid-open Patent Publication No. 2011-52982.

In the automatic urine analyzer of Patent Document 1, there are cases in which the sample dispensing nozzle, having aspirated an urgent sample, passes above a sample in a sample aspiration position on the measurement line. In such cases, some of the urgent sample may fall from the sample dispensing nozzle and contaminate the sample in the sample aspiration position on the measurement line.

Hence it is desired that a sample that has fallen from the nozzle that has aspirated the sample be prevented from contaminating another sample.

According to the embodiments described above, mixing of a sample that has dropped from a nozzle with another sample can be prevented.

The invention claimed is:

1. A sample analyzer, comprising:
a transport mechanism comprising a motor, a belt capable of moving a first sample container, and a pulley around which the belt is wound, the transport mechanism transporting the first sample container to a sample aspiration position;
a setting part in which a second sample container is set, the second sample container accommodating a sample to be measured with priority over measurement of a sample in the first sample container;
a nozzle capable of moving for aspirating the sample from the first sample container at the sample aspiration position and aspirating the sample from the second sample container set in the setting part;
a detector that detects components of the sample aspirated by the nozzle; and,
a controller that, in response to a selection for a sample aspiration from the second sample container using the nozzle at a time when the first sample container is located at the sample aspiration position, is programmed to control the transport mechanism such that the first sample container moves to a position distant from the sample aspiration position, and is programmed to execute control such that the nozzle aspirates the sample from the second sample container and then moves above the sample aspiration position in a state in which the first sample container is located at the position distant from the sample aspiration position, wherein:
the transport mechanism is configured to transport a rack and a second rack, each holding at least one first sample container;
the transport mechanism includes a transport pathway, which includes a rack acceptance position upstream of the aspiration position and a rack ejection position downstream of the aspiration position, and
the controller is programmed to control the transport mechanism such that in response to the selection for the sample aspiration from the second sample container when both the rack and the second rack are positioned on the transport pathway, the transport mechanism moves the rack to the rack ejection position side of the aspiration position and moves the second rack to the rack acceptance position side of the aspiration position.

2. The sample analyzer according to claim 1, wherein:
the detector detects information on particles in a urine sample,
the second sample container accommodates a urine sample as the sample, and
the controller is programmed to execute control such that the nozzle aspirates the urine sample from the second sample container and discharges the aspirated urine sample into the second sample container in order to agitate the urine sample in the second sample container, agitates the urine sample in the second sample container, and then executes control such that the nozzle that has aspirated the agitated urine sample from the second sample container moves above the sample aspiration position.

3. The sample analyzer according to claim 1, wherein the sample aspiration from the second sample container using the nozzle is selected based on receiving an instruction for measurement of the sample in the second sample container.

4. The sample analyzer according to claim 1, further comprising a chamber into which the sample that has been aspirated by the nozzle is discharged, wherein
the sample aspiration position is provided between the setting part and the chamber; and
the controller is programmed to execute a control such that the nozzle, which has aspirated the sample from the second sample container, moves to the chamber, passing above the sample aspiration position in the state in which the first sample container is located at the position distant from the sample aspiration position.

5. The sample analyzer according to claim 1, wherein:
the transport mechanism is configured to transport a rack holding a plurality of first sample containers such that the plurality of first sample containers held in the rack are sequentially transported to the sample aspiration position in order to perform continuous measurements of samples in the plurality of first sample containers; and,
in response to the selection for the sample aspiration from the second sample container during sequentially transporting the plurality of first sample containers held in the rack to the sample aspiration position, the controller is programmed to control the transport mechanism such that transportation of the rack is interrupted and the rack is moved to the position distant from the sample aspiration position.

6. The sample analyzer according to claim 5, wherein, in response to the selection for the sample aspiration from the second sample container during sequentially transporting the first sample containers to the sample aspiration position, the controller is programmed to control the transport mechanism such that when no first sample container remains at the sample aspiration position, the rack on a transport pathway of the transport mechanism moves to the position distant from the sample aspiration position.

7. The sample analyzer according to claim 5, wherein, in response to the selection for the sample aspiration from the second sample container using the nozzle while a next first sample container of the plurality of first sample containers held in the rack from which a next sample is to be aspirated next by the nozzle is being transported to the sample aspiration position, the controller is programmed to continue transport of the rack until the next first sample container from which the next sample is to be aspirated next arrives at the sample aspiration position.

8. The sample analyzer according to claim 5, further comprising:
a first placement region onto which the rack is placed and from which the rack is supplied to the rack acceptance position; and
a second placement region onto which is placed the rack that is ejected from the rack ejection position.

9. The sample analyzer according to claim 5, wherein the controller is programmed to control the transport mechanism such that, after the nozzle, with the sample aspirated from the second sample container, has moved above the sample aspiration position, a next first sample container from which a next sample is to be aspirated next is positioned at the sample aspiration position.

10. The sample analyzer according to claim 5, further comprising a reader, wherein the reader reads out sample information of a next first sample container of the plurality of first sample containers which has been transported, by the transport mechanism, to an information readout position, the controller controls the transport mechanism such that, after the nozzle, with the sample aspirated from the second sample container, has moved above the sample aspiration position, the next first sample container from which sample information is to be read out next is positioned at the information readout position.

11. The sample analyzer according to claim 1, further comprising:

a cover for the setting part; and, a button that receives an instruction to start measurement of the sample of the second sample container, set in the setting part, wherein the cover is configured so as to open when the button receives the instruction; and, when the cover opens, the setting part allows the second sample container to be placed in the setting part.

12. A sample analyzer, comprising:

a transport mechanism comprising a motor, a belt capable of moving a first sample container, and a pulley around which the belt is wound, the transport mechanism transporting the first sample container to a sample aspiration position;

a setting part in which a second sample container is set, the second sample container accommodating a sample to be measured with priority over measurement of a sample in the first sample container;

a nozzle capable of moving for aspirating the sample from the first sample container at the sample aspiration position, and aspirating the sample from the second sample container set in the setting part;

a detector that detects components of a sample aspirated by the nozzle; and, a controller that, in response to a selection for a sample aspiration from the second sample container using the nozzle, determines whether the first sample container is positioned at the sample aspiration position, and when the first sample container is positioned at the sample aspiration position, is programmed to control the transport mechanism such that the first sample container moves to a position distant from the sample aspiration position, and is programmed to execute control such that the nozzle aspirates a sample from the second sample container and then moves above the sample aspiration position in a state in which the first sample container is located at the position distant from the sample aspiration position, wherein:

the transport mechanism is configured to transport a rack and a second rack, each holding at least one first sample container;

the transport mechanism includes a transport pathway, which includes a rack acceptance position upstream of the aspiration position and a rack ejection position downstream of the aspiration position, and the controller is programmed to control the transport mechanism such that in response to the selection for the sample aspiration from the second sample container when both the rack and the second rack are positioned on the transport pathway, the transport mechanism moves the rack to the rack ejection position side of the aspiration position and moves the second rack to the rack acceptance position side of the aspiration position.

13. A transportation apparatus, comprising:

a transport mechanism comprising a motor, a belt capable of moving a first sample container, and a pulley around which the belt is wound, the transport mechanism transporting the first sample container to a sample aspiration position at which a sample is aspirated by a nozzle;

a setting part in which a second sample container is set, the second sample container accommodating a sample to be measured with priority over measurement of the sample in the first sample container; and a controller that, in response to a selection for a sample aspiration from the second sample container using the nozzle and the first sample container has been transported to the sample aspiration position, is programmed to control the transport mechanism such that the first sample container moves to a position distant from the sample aspiration position, and to control the nozzle to aspirate the sample from the second sample container and then move above the sample aspiration position in a state in which the first sample container is located at the position distant from the sample aspiration position, wherein:

the transport mechanism is configured to transport a rack and a second rack, each holding at least one first sample container;

the transport mechanism includes a transport pathway, which includes a rack acceptance position upstream of the aspiration position and a rack ejection position downstream of the aspiration position, and the controller is programmed to control the transport mechanism such that in response to the selection for the sample aspiration from the second sample container when both the rack and the second rack are positioned on the transport pathway, the transport mechanism moves the rack to the rack ejection position side of the aspiration position and moves the second rack to the rack acceptance position side of the aspiration position.

* * * * *